(12) United States Patent
Lindsley et al.

(10) Patent No.: US 8,497,289 B2
(45) Date of Patent: Jul. 30, 2013

(54) 3.1.0 BICYCLIC GLYT1 INHIBITORS AND METHODS OF MAKING AND USING SAME

(75) Inventors: Craig W. Lindsley, Brentwood, TN (US); P. Jeffrey Conn, Brentwood, TN (US); Richard Williams, Bangor (GB); Carrie K. Jones, Nashville, TN (US); Douglas J. Sheffler, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 487 days.

(21) Appl. No.: 12/648,972

(22) Filed: Dec. 29, 2009

(65) Prior Publication Data

US 2010/0256192 A1 Oct. 7, 2010

Related U.S. Application Data

(60) Provisional application No. 61/141,030, filed on Dec. 29, 2008.

(51) Int. Cl.
*A61K 31/44* (2006.01)
*C07D 403/02* (2006.01)

(52) U.S. Cl.
USPC ...... 514/339; 514/398; 548/314.7; 546/276.7

(58) Field of Classification Search
USPC .............. 514/339, 398; 548/314.7; 546/276.7
See application file for complete search history.

(56) References Cited

U.S. PATENT DOCUMENTS 5,981,168 A * 11/1999 Reiner et al. ............... 435/4
2008/0319043 A1 12/2008 Salman et al.

FOREIGN PATENT DOCUMENTS

WO WO-2005/037216 4/2005
WO WO 2007/060484 5/2007

OTHER PUBLICATIONS

Extended European Search Report for corresponding EP Application No. 09837121.4, mailed Jun. 29, 2012.
Ohno et al., "Novel Synthesis of 3-Azabicyclo[3.1.0]hexanes by unusual palladium (0)-catalyzed cyclopropanation of allenese," Organic Letters 5(25):4763-4766 (2003).

* cited by examiner

*Primary Examiner* — Rei-tsang Shiao
(74) *Attorney, Agent, or Firm* — Choate, Hall & Stewart, LLP; Andrea L. C. Robidoux; Xiaodong Li

(57) ABSTRACT

In one aspect, the invention relates to compounds which are useful as inhibitors of glycine type 1 transporter (GlyT1) activity; synthetic methods for making the compounds; pharmaceutical compositions comprising the compounds; and methods of treating disorders associated with glycine type 1 transporter (GlyT1) activity using the compounds and compositions. This abstract is intended as a scanning tool for purposes of searching in the particular art and is not intended to be limiting of the present invention.

8 Claims, No Drawings

3.1.0 BICYCLIC GLYT1 INHIBITORS AND METHODS OF MAKING AND USING SAME

CROSS-REFERENCE TO RELATED APPLICATIONS

This application claims the benefit of U.S. Application No. 61/141,030, filed Dec. 29, 2008, which is hereby incorporated herein by reference in its entirety.

BACKGROUND

Schizophrenia is a debilitating psychiatric disorder characterized by a combination of negative (blunted affect, withdrawal, anhedonia) and positive (paranoia, hallucinations, delusions) symptoms as well as marked cognitive deficits. While the etiology of schizophrenia is currently unknown, the disease appears to be produced by a complex interaction of biological, environmental, and genetic factors. Over 40 years ago it was found that phencyclidine (PCP) induces a psychotic state in humans that is very similar to that observed in schizophrenic patients. The finding that the main mode of action of PCP is that of a non-competitive antagonist of the N-methyl-D-aspartate (NMDA) subtype of ionotropic glutamate receptor stimulated a series of studies that have led to the development of the NMDA receptor hypofunction model of schizophrenia (Jentsch J D and Roth R H, 1999 Neuropsychopharmacology, 20:201).

Fast glutamatergic transmission in the mammalian central nervous system is primarily mediated by the excitatory amino acid glutamate acting on ionotropic glutamate receptors (iGluRs). The iGluRs are comprised of three major subclasses, including the α-amino-3-hydroxy-5-methyl-4-isoxazolepropionic acid (AMPA), kainate, and NMDA receptor subtypes (Hollmann M and Heinemann S, 1994, Annu. Rev. Neurosci. 17:31). These three subclasses are multimeric ligand-gated cation channels which open in response to glutamate binding to induce a depolarizing excitatory post synaptic current. Molecular cloning has revealed that the NMDA receptor family is composed of two primary subunits, NR1 and NR2. In addition a novel inhibitory subunit which is developmentally regulated termed NR3 has been recently described. A high degree of molecular diversity exists within each set of subunits. To date, only one NR1 subunit gene has been cloned; however, alternative splicing of the NR1 gene can produce eight different subunits. In contrast, 4 genes have been cloned for the NR2 subunit (NR2A, NR2B, NR2C, and NR2D), some of which exhibit alternative splicing (Hollmann M and Heinemann S, 1994, Annu. Rev. Neurosci. 17:31). These multiple subunits form heteromeric glutamate-gated ion channels. While the precise subunit stoichiometry of the naturally occurring receptor remains unknown, both the NR1 and NR2 subunits are required for the expression of functionally active receptor-channel complexes in mammalian expression systems.

Activation of the NMDA receptor requires the binding of both glutamate and glycine (Johnson J W and Ascher P, 1987, Nature 325:529). Interestingly, the binding sites for these two co-agonists exist on separate subunits as determined by site-directed mutagenesis studies (Laube B, Hirai H, Sturgess M, Betz H and Kuhse J, 1997, Neuron 18:493). On the NR2A and NR2B subunits, a binding pocket for glutamate is formed by interactions between the N-terminus of the receptor and the extracellular loops. Analogous experiments have placed the glycine binding site in a homologous region of the NR1 subunit (Kuryatov A, Laube B, Betz H and Kuhse J, 1994, Neuron 12:1291). Depending on the actual subunit composition, glutamate and glycine activate the NMDA receptor with EC50 values in the high nanomolar to low micromolar range. In addition, the pore of the NMDA receptor is impermeable to magnesium. Under normal resting conditions, extracellular magnesium can bind to a site within the pore and produce a magnesium block of the channel. This magnesium block imparts a voltage dependence to the channel which allows the NMDA receptor to act as a coincidence detector requiring the binding of glutamate, glycine, and the occurrence of postsynaptic depolarization before conducting current. Of particular interest is the finding that the psychotomimetic drugs MK-801, PCP, and ketamine all act as open channel blockers of the NMDA receptor-channel by binding to a site that overlaps with the magnesium binding site. It is apparent that the rich diversity of NMDA receptor subunits and regulatory sites provides for a complex assortment of physiologically and pharmacologically distinct heteromeric receptors making the NMDA receptor an ideal target for the design of novel therapeutic compounds.

The NMDA receptor plays a critical role in a variety of neurophysiological phenomena, including but not limited to synaptic plasticity, cognition, attention and memory (Bliss T and Collingridge W, 1993, Nature 361:31; Morris R G M et al., 1986, Nature 319:774). Psychotomimetic drugs constitute a wide class of drugs including psychomotor stimulants (cocaine, amphetamine), hallucinogens (LSD), and NMDA receptor antagonists (PCP, ketamine). Of these, only the NMDA receptor antagonists appear to elicit a robust induction of the positive, negative, and cognitive symptoms of schizophrenia. Controlled studies of ketamine-induced psychosis in human subjects, as well as observations of symptoms from patients abusing PCP as a recreational drug, have produced a convincing list of similarities between NMDA receptor antagonist-induced psychosis and schizophrenia (Jentsch J D and Roth R H, 1999 Neuropsychopharmacology, 20:201). NMDA-receptor antagonists faithfully mimic the symptoms of schizophrenia to the extent that it is difficult to differentiate the two in the clinic. In addition, NMDA receptor antagonists can exacerbate the symptoms in schizophrenics, and can trigger the re-emergence of symptoms in stable patients. Finally, the finding that NMDA receptor co-agonists such as glycine, D-cycloserine, and D-serine produce benefits in schizophrenic patients implicates NMDA receptor hypofunction in this disorder, and indicate that increasing NMDA receptor activation may provide a therapeutic benefit (Leiderman E et al., 1996, Biol. Psychiatry 39:213, Javitt D C et al., 1994, Am. J. Psychiatry 151:1234, Heresco-Levy U, 2000, Int. J. Neuropsychopharmacol. 3:243, Tsai G et al., 1998, Biol. Psychiatry 44:1081). A large number of studies in animal models lend support to the NMDA hypofunction hypothesis of schizophrenia. Generation of a mutant mouse expressing only 5% of normal levels of the NMDA NR1 subunit have shown that this decrease in functional NMDA receptors induces a state very similar to that observed in other animal models of schizophrenia (Mohn A R et al., 1999, Cell 98:427). Besides schizophrenia, dysfunction of glutamatergic pathways has been implicated in a number of disease states in the human central nervous system (CNS) including but not limited to cognitive deficits, dementia, Parkinson disease, Alzheimer disease and bipolar disorder.

NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses. Clinical trials in which high doses of glycine were administered orally as an add-on to standard neuroleptic therapy showed an improvement of the symptoms of schizophrenia patients (Javitt et al. Int. J. Neuropsychopharmacol. (2001) 4: 385-391). One way to increase synaptic glycine levels without administering exogenous glycine is to inhibit its removal from the synapse. Evidence that this approach would be useful in treating schizophrenia comes from a double-blind placebo controlled study in which sarcosine was administered to patients suffering from schizophrenia, but who were poorly responsive to antipsychotic drugs. A beneficial effect was observed on positive, negative and cognitive symptoms, indicating that inhibition of glycine re-uptake is a reasonable approach to the treatment of schizophrenia.

Two specific glycine transporters, GlyT1 and GlyT2 have been identified and shown to belong to the $Na^+/Cl^-$ dependent family of neurotransmitter transporters which includes taurine, γ-aminobutyric acid (GABA), proline, monoamines and orphan transporters (Smith K E et al., 1992, Neuron 8:927; Borowsky B et al., 1993, Neuron 10:851; Liu Q R et al., 1993, J. Biol. Chem. 268:22802; Kim K M et al., 1994, Mol. Pharmacol. 45:608; Morrow J A et al., 1998, FEBS Lett. 439:334; Nelson N, 1998, J. Neurochem. 71:1785). GlyT1 and GlyT2 have been isolated from different species and shown to have only 50% identity at the amino acid level. They also have a different pattern of expression in mammalian central nervous system with GlyT2 being expressed in spinal cord, brainstem and cerebellum and GlyT1 present in these regions as well as forebrain areas such as cortex, hippocampus, septum and thalamus (Smith K E et al., 1992, Neuron 8:927; Borowsky B et al., 1993, Neuron 10:851; Liu Q R et al., 1993, J. Biol. Chem. 268:22802). At the cellular level, GlyT2 has been reported to be expressed by glycinergic nerve endings in rat spinal cord whereas GlyT1 appears to be preferentially expressed by glial cells (Zafra F et al., 1995, J. Neurosci. 15:3952). These expression studies have led to the conclusion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxy)propyl])sarcosine (NFPS) potentiates NMDA receptor activity and NMDA receptor-dependent long-term potentiation in rat (Bergeron, R. et al., 1998, PNAS USA 95:15730; Kinney, G. et al., 2003, J. Neurosci. 23:7586). Furthermore, NFPS has been reported to enhance pre-pulse inhibition in mice, a measure of sensory gating that is known to be deficient in schizophrenia patients (Kinney G et al., 2003, J. Neurosci. 23:7586). These physiological effects of GlyT1 in forebrain regions together with clinical reports showing the beneficial effects of GlyT1 inhibitor sarcosine in improving symptoms in schizophrenia patients (Tsai and Coyle, WO99/52519) indicate that selective GlyT1 uptake inhibitors represent a new class of antipsychotic drugs.

Despite advances in GlyT1 uptake inhibitor research, there is still a scarcity of compounds that effectively inhibit the glycine transporter GlyT1 that are also effective in the treatment of neurological and psychiatric disorders associated with glutamatergic neurotransmission dysfunction and diseases in which the glycine transporter GlyT1 is involved. These needs and other needs are addressed by the present invention.

SUMMARY

In accordance with the purpose(s) of the invention, as embodied and broadly described herein, the invention, in one aspect, relates to compounds useful as inhibitors of glycine type 1 transporter (GlyT1) activity, methods of making same, pharmaceutical compositions comprising same, and methods of treating disorders associated with glycine type 1 transporter (GlyT1) activity.

Disclosed are compounds having a structure represented by a formula:

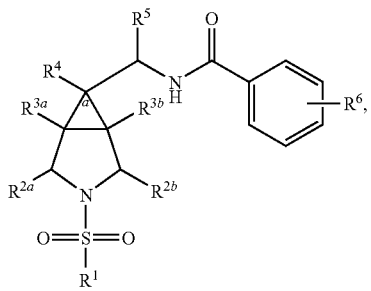

wherein $R^1$ is optionally substituted organic residue comprising 1 to 12 carbon atoms; wherein each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, $N(R)_2$, and optionally substituted organic residue comprising 1 to 12 carbons; wherein $R^5$ comprises two substituents independently selected from hydrogen, halogen, OR, cyano, nitro, SR, $N(R)_2$, and optionally substituted organic residue comprising 1 to 6 carbons; wherein $R^6$ comprises five substituents independently selected from hydrogen, halogen, OR, cyano, nitro SR, $N(R)_2$, and optionally substituted organic residue comprising from 1 to 6 carbon atoms; or a pharmaceutically acceptable derivative thereof.

Also disclosed are methods for preparing a compound comprising the step of reacting a first compound or derivative thereof having a structure represented by a formula:

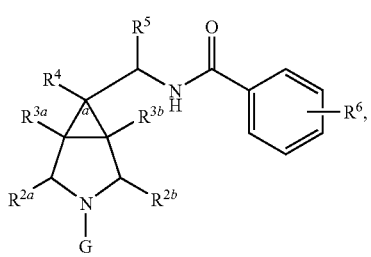

wherein each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, $N(R)_2$, and optionally substituted organic residue comprising 1 to 12 carbons; wherein $R^5$ comprises two substituents independently selected from hydrogen, halogen, OR, cyano, nitro, SR, $N(R)_2$, and optionally substituted organic residue comprising 1 to 6 carbons; wherein $R^6$ comprises five substituents independently selected from hydrogen, halogen, OR, cyano, nitro SR, $N(R)_2$, and optionally substituted organic residue comprising from 1 to 6 carbon atoms; wherein G is hydrogen or a protecting group; with a second compound having a structure represented by a formula:

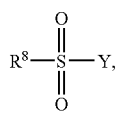

wherein $R^8$ is an optionally substituted organic residue comprising 1 to 12 carbon atoms; and wherein Y is a leaving group.

Also disclosed are methods for preparing a compound comprising the step of reacting a first compound or derivative thereof having a structure represented by a formula:

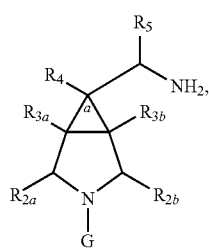

wherein each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, $N(R)_2$, and optionally substituted organic residue comprising 1 to 12 carbons; wherein $R^5$ comprises two substituents independently selected from hydrogen, halogen, OR, cyano, nitro, SR, $N(R)_2$, and optionally substituted organic residue comprising 1 to 6 carbons; wherein G is hydrogen, a protecting group, or a structure represented by a formula:

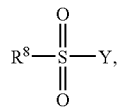

wherein $R^8$ is an optionally substituted organic residue comprising 1 to 12 carbon atoms; with a second compound, or synthetic equivalent thereof, having a structure represented by a formula:

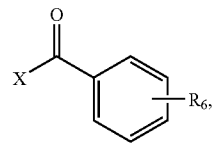

wherein $R^6$ comprises five substituents independently selected from hydrogen, halogen, OR, cyano, nitro SR, $N(R)_2$, and optionally substituted organic residue comprising from 1 to 6 carbon atoms; and wherein X is a leaving group.

Also disclosed are methods for inhibiting glyT1 activity in at least one cell comprising the step of contacting the at least one cell with at least one compound having a structure represented by a formula:

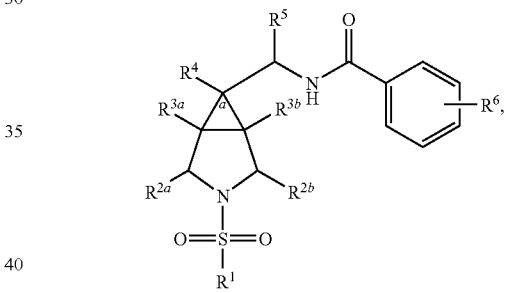

wherein $R^1$ is optionally substituted organic residue comprising 1 to 12 carbon atoms; wherein each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, $N(R)_2$, and optionally substituted organic residue comprising 1 to 12 carbons; wherein $R^5$ comprises two substituents independently selected from hydrogen, halogen, OR, cyano, nitro, SR, $N(R)_2$, and optionally substituted organic residue comprising 1 to 6 carbons; wherein $R^6$ comprises five substituents independently selected from hydrogen, halogen, OR, cyano, nitro SR, $N(R)_2$, and optionally substituted organic residue comprising from 1 to 6 carbon atoms; or a pharmaceutically acceptable derivative thereof, in an amount effective to inhibit glyT1 receptor activity in the at least one cell.

Also disclosed are methods for inhibiting glyT1 activity in a subject comprising the step of administering to the subject a therapeutically effective amount of at least one compound having a structure represented by a formula:

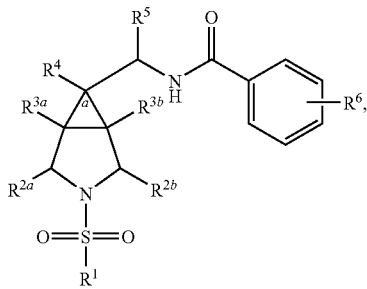

wherein $R^1$ is optionally substituted organic residue comprising 1 to 12 carbon atoms; wherein each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, $N(R)_2$, and optionally substituted organic residue comprising 1 to 12 carbons; wherein $R^5$ comprises two substituents independently selected from hydrogen, halogen, OR, cyano, nitro, SR, $N(R)_2$, and optionally substituted organic residue comprising 1 to 6 carbons; wherein $R^6$ comprises five substituents independently selected from hydrogen, halogen, OR, cyano, nitro SR, $N(R)_2$, and optionally substituted organic residue comprising from 1 to 6 carbon atoms; or a pharmaceutically acceptable derivative thereof, in a dosage and amount effective to inhibit glyT1 receptor activity in the subject.

Also disclosed are methods for the treatment of a disorder associated with glycinergic or glutamatergic neurotransmission dysfunction in a mammal comprising the step of administering to the mammal at least one compound having a structure represented by a formula:

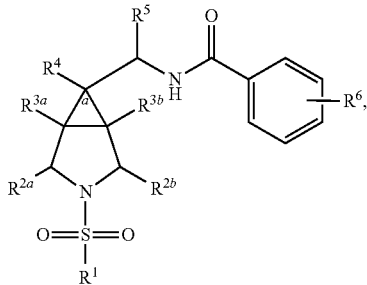

wherein $R^1$ is optionally substituted organic residue comprising 1 to 12 carbon atoms; wherein each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, $N(R)_2$, and optionally substituted organic residue comprising 1 to 12 carbons; wherein $R^5$ comprises two substituents independently selected from hydrogen, halogen, OR, cyano, nitro, SR, $N(R)_2$, and optionally substituted organic residue comprising 1 to 6 carbons; wherein $R^6$ comprises five substituents independently selected from hydrogen, halogen, OR, cyano, nitro SR, $N(R)_2$, and optionally substituted organic residue comprising from 1 to 6 carbon atoms; or a pharmaceutically acceptable derivative thereof, in a dosage and amount effective to treat the disorder in the mammal.

Also disclosed are methods for the manufacture of a medicament for inhibition of glyT1 receptor activity in a mammal comprising combining at least one compound having a structure represented by a formula:

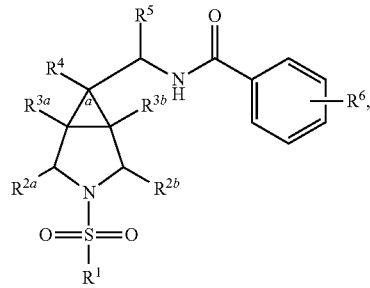

wherein $R^1$ is optionally substituted organic residue comprising 1 to 12 carbon atoms; wherein each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, $N(R)_2$, and optionally substituted organic residue comprising 1 to 12 carbons; wherein $R^5$ comprises two substituents independently selected from hydrogen, halogen, OR, cyano, nitro, SR, $N(R)_2$, and optionally substituted organic residue comprising 1 to 6 carbons; wherein $R^6$ comprises five substituents independently selected from hydrogen, halogen, OR, cyano, nitro SR, $N(R)_2$, and optionally substituted organic residue comprising from 1 to 6 carbon atoms; or a pharmaceutically acceptable derivative thereof, with a pharmaceutically acceptable carrier.

Also disclosed are the products of the disclosed methods.

Also disclosed are pharmaceutical compositions comprising the disclosed compounds and/or disclosed products, and a pharmaceutically acceptable carrier.

Also disclosed are methods for inhibiting glyT1 activity in at least one cell comprising the step of contacting the at least one cell with at least one disclosed compound and/or product in an amount effective to inhibit glyT1 receptor activity in the at least one cell.

Also disclosed are methods for inhibiting glyT1 activity in a subject comprising the step of administering to the subject a therapeutically effective amount of at least one disclosed compound and/or product, in a dosage and amount effective to inhibit glyT1 receptor activity in the subject.

Also disclosed are methods for the treatment of a disorder associated with glycinergic or glutamatergic neurotransmission dysfunction in a mammal comprising the step of administering to the mammal at least one disclosed compound and/or product, in a dosage and amount effective to treat the disorder in the mammal.

Also disclosed are methods for the manufacture of a medicament for inhibition of glyT1 receptor activity in a mammal comprising combining at least one disclosed compound and/or product with a pharmaceutically acceptable carrier.

Also disclosed are uses of at least one compound having a structure represented by a formula:

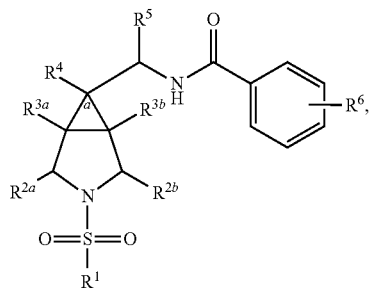

wherein $R^1$ is optionally substituted organic residue comprising 1 to 12 carbon atoms; wherein each $R^{2a}$ and $R^{2b}$ comprises two substituents independently selected from hydrogen, halogen, OR, nitrile, nitro, SR, N(R)$_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, N(R)$_2$, and optionally substituted organic residue comprising 1 to 12 carbons; wherein $R^5$ comprises two substituents independently selected from hydrogen, halogen, OR, cyano, nitro, SR, N(R)$_2$, and optionally substituted organic residue comprising 1 to 6 carbons; wherein $R^6$ comprises five substituents independently selected from hydrogen, halogen, OR, cyano, nitro SR, N(R)$_2$, and optionally substituted organic residue comprising from 1 to 6 carbon atoms; or a pharmaceutically acceptable derivative thereof, for inhibition of glyT1 receptor activity in a mammal.

Also disclosed are kits comprising at least one compound having a structure represented by a formula:

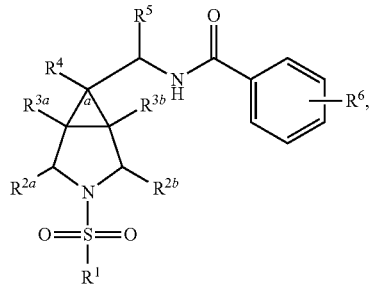

wherein $R^1$ is optionally substituted organic residue comprising 1 to 12 carbon atoms; wherein each $R^{2a}$ and $R^{2b}$ comprises two substituents independently selected from hydrogen, halogen, OR, nitrile, nitro, SR, N(R)$_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, N(R)$_2$, and optionally substituted organic residue comprising 1 to 12 carbons; wherein $R^5$ comprises two substituents independently selected from hydrogen, halogen, OR, cyano, nitro, SR, N(R)$_2$, and optionally substituted organic residue comprising 1 to 6 carbons; wherein $R^6$ comprises five substituents independently selected from hydrogen, halogen, OR, cyano, nitro SR, N(R)$_2$, and optionally substituted organic residue comprising from 1 to 6 carbon atoms; or a pharmaceutically acceptable derivative thereof, and one or more of: a. at least one agent known to increase glyT1 receptor activity; b. at least one agent known to decrease glyT1 receptor activity; c. at least one agent known to treat a glutamatergic neurotransmission dysfunction; or d. instructions for treating a disorder associated with glutamatergic neurotransmission dysfunction.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by inhibition of GlyT1 activity" means having been subjected to a physical examination by a person of skill, for example, a physician, and found to have a condition that can be diagnosed or treated by a compound or composition that can favorably inhibit GlyT1 activity. As a further example, "diagnosed with a need for inhibition of GlyT1 activity" refers to having been subjected to a physical examination by a person of skill, for example, a physician, and found to have a condition characterized by excessive GlyT1 activity. Such a diagnosis can be in reference to a disorder, such as psychiatric disorder, obesity, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to GlyT1 activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, in some embodiments, the present invention provides a single unit dosage form comprising a disclosed compound and/or product, an additional therapeutic agent, and a pharmaceutically acceptable carrier, adjuvant, or vehicle.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B.

and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some aspects, aliphatic groups contain 1-5 aliphatic carbon atoms. In other aspects, aliphatic groups contain 1-4 aliphatic carbon atoms. In still other aspects, aliphatic groups contain 1-3 aliphatic carbon atoms, and in yet other aspects, aliphatic groups contain 1-2 aliphatic carbon atoms. In some aspects, "cycloaliphatic" (or "carbocycle" or "cycloalkyl") refers to a monocyclic C3-C6 hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated," as used herein, means that a moiety has one or more units of unsaturation.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. Exemplary lower alkyl groups are methyl, ethyl, propyl, isopropyl, butyl, isobutyl, and tert-butyl. The term "lower haloalkyl" refers to a C1-C6 (e.g., C1-C4) straight or branched alkyl group that is substituted with one or more halogen atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or $OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain aspects of the present invention, "aryl" refers to an aromatic ring system which includes, but is not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The term "aryl" includes, but is not limited to, benzene, naphthalene, phenyl, biphenyl, phenoxybenzene, and the like. The term "aryl" also includes "heteroaryl." The term "aryl" also includes "non-heteroaryl," which defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl). In some aspects, "heterocycle," includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$— where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$_2A^1$, or —OS(O)$_2$O$A^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

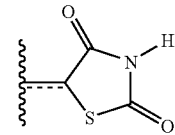

regardless of whether thiazolidinedione is used to prepare the compound. In some aspects the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some aspects, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0\text{-}4}R^\circ$; —$(CH_2)_{0\text{-}4}OR^\circ$; —$O(CH_2)_{0\text{-}4}R^\circ$, —O—$(CH_2)_{0\text{-}4}C(O)OR^\circ$; —$(CH_2)_{0\text{-}4}CH(OR^\circ)_2$; —$(CH_2)_{0\text{-}4}SR^\circ$; —$(CH_2)_{0\text{-}4}Ph$, which may be substituted with $R^\circ$; —$(CH_2)_{0\text{-}4}O(CH_2)_{0\text{-}1}Ph$ which may be substituted with $R^\circ$; —CH=CHPh, which may be substituted with $R^\circ$; —$(CH_2)_{0\text{-}4}O(CH_2)_{0\text{-}1}$-pyridyl which may be substituted with $R^\circ$; —$NO_2$; —CN; —$N_3$; —$(CH_2)_{0\text{-}4}N(R^\circ)_2$; —$(CH_2)_{0\text{-}4}N(R^\circ)C(O)R^\circ$; —$N(R^\circ)C(S)R^\circ$; —$(CH_2)_{0\text{-}4}N(R^\circ)C(O)NR^\circ_2$; —$N(R^\circ)C(S)NR^\circ_2$; —$(CH_2)_{0\text{-}4}N(R^\circ)C(O)OR^\circ$; —$N(R^\circ)N$ $(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0\text{-}4}C(O)R^\circ$; —$C(S)R^\circ$; —$(CH_2)_{0\text{-}4}C(O)OR^\circ$; —$(CH_2)_{0\text{-}4}C(O)SR^\circ$; —$(CH_2)_{0\text{-}4}OC(O)R^\circ$; —$OC(O)(CH_2)_{0\text{-}4}SR$—, $SC(S)SR^\circ$; —$(CH_2)_{0\text{-}4}SC(O)R^\circ$; —$(CH_2)_{0\text{-}4}C(O)NR^\circ_2$; —$C(S)NR^\circ_2$; —$C(S)SR^\circ$; —$SC(S)SR^\circ$, —$(CH_2)_{0\text{-}4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0\text{-}4}SSR^\circ$; —$(CH_2)_{0\text{-}4}S(O)_2R^\circ$; —$(CH_2)_{0\text{-}4}S(O)_2OR^\circ$; —$(CH_2)_{0\text{-}4}OS(O)_2R^\circ$; —$S(O)_2NR^\circ_2$; —$(CH_2)_{0\text{-}4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1\text{-}4}$ straight or branched)alkylene)O—$N(R^\circ)_2$; or —$(C_{1\text{-}4}$ straight or branched alkylene)C(O)O—$N(R^\circ)_2$, wherein each $R^\circ$ may be substituted as defined below and is independently hydrogen, $C_{1\text{-}6}$ aliphatic, —$CH_2Ph$, —$O(CH_2)_{0\text{-}1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0\text{-}2}R^\bullet$, -(halo$R^\bullet$), —$(CH_2)_{0\text{-}2}OH$, —$(CH_2)_{0\text{-}2}OR^\bullet$, —$(CH_2)_{0\text{-}2}CH(OR^\bullet)_2$; —$O(haloR^\bullet)$, —CN, —$N_3$, —$(CH_2)_{0\text{-}2}C(O)R^\bullet$, —$(CH_2)_{0\text{-}2}C(O)OH$, —$(CH_2)_{0\text{-}2}C(O)OR^\bullet$, —$(CH_2)_{0\text{-}2}SR^\bullet$, —$(CH_2)_{0\text{-}2}SH$, —$(CH_2)_{0\text{-}2}NH_2$, —$(CH_2)_{0\text{-}2}NHR^\bullet$, —$(CH_2)_{0\text{-}2}NR^\bullet_2$, —$NO_2$, —$SiR^\bullet_3$, —$OSiR^\bullet_3$, —$C(O)SR^\bullet$, —$(C_{1\text{-}4}$ straight or branched alkylene)C(O)OR$^\bullet$, or —$SSR^\bullet$ wherein each $R^\bullet$ is unsubstituted or where preceded by "halo" is substituted only with one or more halogens, and is independently selected from $C_{1\text{-}4}$ aliphatic, —$CH_2Ph$, —$O(CH_2)_{0\text{-}1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2\text{-}3}O$—, or —$S(C(R^*_2))_{2\text{-}3}S$—, wherein each independent occurrence of $R^*$ is selected from hydrogen, $C_{1\text{-}6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2\text{-}3}O$—, wherein each independent occurrence of $R^*$ is selected from hydrogen, $C_{1\text{-}6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^\bullet$, -(halo$R^\bullet$), —OH, —$OR^\bullet$, —$O(haloR^\bullet)$, —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1\text{-}4}$ aliphatic, —$CH_2Ph$, —$O(CH_2)_{0\text{-}1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of this invention. Such compounds are useful, for example, as analytical tools, as probes in biological assays, or as therapeutic agents in accordance with the present invention.

The term "hydrolysable residue" is meant to refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "leaving group" refers to an atom (or a group of atoms) with electron withdrawing ability that can be displaced as a stable species, taking with it the bonding electrons. Examples of suitable leaving groups include sulfonate esters, including, but not limited to, triflate, mesylate, tosylate, brosylate, and halides.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable minor images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (ee). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are minor image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

In some aspects, a structure of a compound can be represented by a formula:

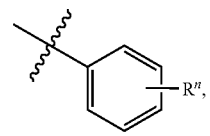

which is understood to be equivalent to a formula:

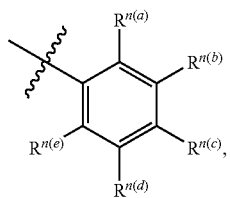

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds, or pharmaceutically acceptable derivatives thereof, useful as inhibitors of glycine type 1 transporter (GlyT1) activity. In general, it is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to compounds having a structure represented by a formula:

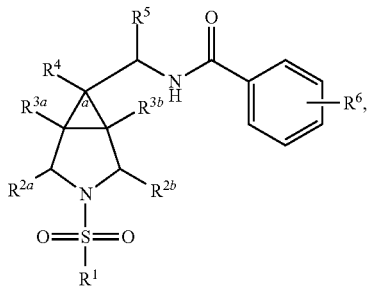

wherein $R^1$ is optionally substituted organic residue comprising 1 to 12 carbon atoms; wherein each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, $N(R)_2$, and optionally substituted organic residue comprising 1 to 12 carbons; wherein $R^5$ comprises two substituents independently selected from hydrogen, halogen, OR, cyano, nitro, SR, $N(R)_2$, and optionally substituted organic residue comprising 1 to 6 carbons; wherein $R^6$ comprises five substituents independently selected from hydrogen, halogen, OR, cyano, nitro SR, $N(R)_2$, and optionally substituted organic residue comprising from 1 to 6 carbon atoms; or a pharmaceutically acceptable derivative thereof. In a further aspect, the carbon at position "a" has a stereochemistry of R or S.

In a further aspect, a compound can have a structure represented by a formula:

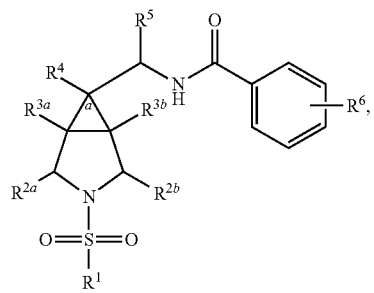

wherein $R^1$ is optionally substituted organic residue comprising 1 to 12 carbon atoms; wherein each $R^{2a}$ and $R^{2b}$ comprises two substituents independently selected from hydrogen, halogen, hydroxyl, nitrile, nitro, thiol, optionally substituted amino, and optionally substituted organic residue comprising from 1 to 6 carbons; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, hydroxyl, cyano, nitro, thiol, amino, and optionally substituted organic residue comprising 1 to 12 carbons; wherein $R^5$ comprises two substituents independently selected from hydrogen, halogen, hydroxyl, cyano, nitro, thiol, amino, and optionally substituted organic residue comprising 1 to 6 carbons; wherein $R^6$ comprises five substituents independently selected from hydrogen, halogen, hydroxyl, cyano, nitro, thiol, amino, and optionally substituted organic residue comprising from 1 to 6 carbon atoms. In a further aspect, the carbon at position "a" has a stereochemistry of R or S; or a pharmaceutically acceptable derivative thereof.

In a further aspect, $R^1$ is selected from optionally substituted C1-C12 alkyl or C2-C12 alkenyl or C2-C12 alkynyl, optionally substituted C1-C12 heteroalkyl or C2-C12 heteroalkenyl or C2-C12 heteroalkynyl, optionally substituted C3-C12 cycloalkyl or C3-C12 cycloalkenyl, optionally substituted C3-C12 heterocycloalkyl or C3-C12 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, and alkylamine-carbonyl.

In a further aspect, $R^{2a}$ and $R^{2b}$ are independently selected from hydrogen and optionally substituted organic residue comprising from 1 to 6 carbons. In a further aspect, both $R^{2a}$ and $R^{2b}$ are hydrogen. In a further aspect, both $R^{3a}$ and $R^{3b}$ are hydrogen.

In a further aspect, $R^4$ is selected from C1-C12 alkyl or C2-C12 alkenyl or C2-C12 alkynyl, optionally substituted C1-C12 heteroalkyl or C2-C12 heteroalkenyl or C2-C12 heteroalkynyl, optionally substituted C3-C12 cycloalkyl or C3-C12 cycloalkenyl, optionally substituted C3-C12 heterocycloalkyl or C3-C12 heterocycloalkenyl, optionally substituted aryl, optionally substituted heteroaryl.

In a further aspect, each $R^5$ is hydrogen.

In a further aspect, each $R^6$ is independently selected from hydrogen, halogen, and optionally substituted organic residue comprising from 1 to 6 carbons.

In a further aspect, the compound has a structure represented by a formula:

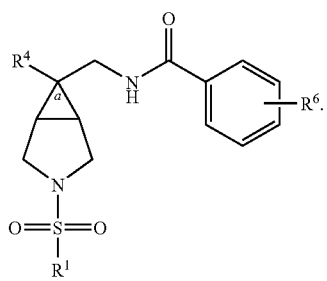

In a further aspect, R is selected from optionally substituted C1-C12 alkyl or C2-C12 alkenyl or C2-C12 alkynyl, optionally substituted C1-C12 heteroalkyl or C2-C12 heteroalkenyl or C2-C12 heteroalkynyl, optionally substituted C3-C12 cycloalkyl or C3-C12 cycloalkenyl, optionally substituted C3-C12 heterocycloalkyl or C3-C12 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, aminocarbonyl, and alkylamine-carbonyl.

In a further aspect, $R^4$ is selected from C1-C12 alkyl or C2-C12 alkenyl or C2-C12 alkynyl, optionally substituted C1-C12 heteroalkyl or C2-C12 heteroalkenyl or C2-C12 heteroalkynyl, optionally substituted C3-C12 cycloalkyl or C3-C12 cycloalkenyl, optionally substituted C3-C12 heterocycloalkyl or C3-C12 heterocycloalkenyl, optionally substituted aryl, optionally substituted heteroaryl. In a further aspect, $R^4$ is optionally substituted C3-C12 cycloalkyl. In a further aspect, $R^4$ is optionally substituted heteroaryl. In a further aspect, $R^4$ is optionally substituted pyridyl. In a further aspect, $R^4$ is optionally substituted 2-pyridyl.

In a further aspect, each $R^6$ is independently selected from hydrogen, halogen, and optionally substituted organic residue comprising from 1 to 6 carbons.

In a further aspect, $R^1$ is selected from optionally substituted C3-C11 cycloalkyl or C3-C11 cycloalkenyl or C6-C11 cycloalkynyl, optionally substituted C3-C10 heterocycloalkyl or C3-C10 heterocycloalkenyl or C6-C10 heterocycloalkynyl, optionally substituted aryl, optionally substituted heteroaryl, and optionally substituted heterocycle. In a further aspect, $R^1$ is optionally substituted heterocycle selected from pyridinyl, pyrimidinyl, furanyl, thiophenyl, pyrrolyl, isoxazolyl, isothiazolyl, pyrazolyl, oxazolyl, thiazolyl, imidazolyl, and oxazolyl. In a further aspect, $R^1$ is optionally substituted heterocycle selected from 1,2,3-oxadiazolyl, 1,2,5-oxadiazolyl and 1,3,4-oxadiazolyl, and thiadiazolyl. In a further aspect, $R^1$ is optionally substituted heterocycle selected from 1,2,3-thiadiazolyl, 1,2,5-thiadiazolyl, and 1,3,4-thiadiazolyl, and triazolyl. In a further aspect, $R^1$ is optionally substituted heterocycle selected from 1,2,3-triazolyl, 1,3,4-triazolyl, and tetrazolyl. In a further aspect, $R^1$ is optionally substituted heterocycle selected from 1,2,3,4-tetrazolyl and 1,2,4,5-tetrazolyl, pyridinyl, pyridazinyl, pyrimidinyl, pyrazinyl, triazinyl, including 1,2,4-triazinyl and 1,3,5-triazinyl, and tetrazinyl. In a further aspect, $R^1$ is optionally substituted heterocycle selected from 1,2,4,5-tetrazinyl, pyrrolidinyl, piperidinyl, piperazinyl, morpholinyl, azetidinyl, tetrahydropyranyl, tetrahydrofuranyl, and dioxanyl. In a further aspect, $R^1$ is 1-methyl-1H-imidazolyl.

In one aspect, the compound has a structure represented by a formula:

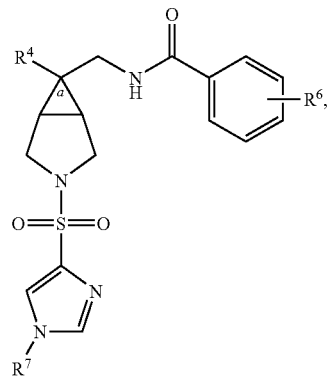

wherein $R^7$ is hydrogen or optionally substituted organic residue comprising from 1 to 9 carbons. In a further aspect, $R^7$ is selected from methyl, ethyl, n-propyl, i-propyl, cyclopropyl, n-butyl, i-butyl, s-butyl, pentyl, hexyl, heptyl, octyl, nonyl, phenyl, and benzyl.

In a further aspect, the compound has a structure represented by a formula:

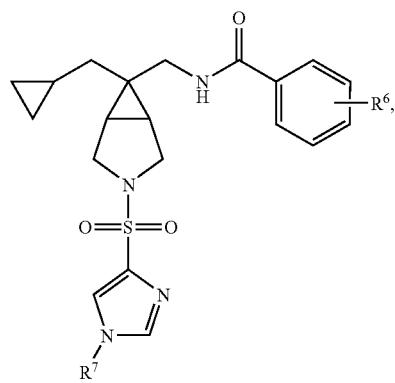

wherein $R^7$ is selected from methyl, ethyl, n-propyl, i-propyl, cyclopropyl, n-butyl, i-butyl, s-butyl, pentyl, hexyl, heptyl, octyl, nonyl, phenyl, and benzyl. In a further aspect, $R^7$ is methyl. In a further aspect, at least one of $R^6$ is halogen.

a. R Groups

In one aspect, each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur.

b. $R^1$ Groups

In one aspect, R is an optionally substituted organic residue comprising from 1 to 12 carbons.

In a further aspect, $R^1$ is an optionally substituted group selected from C1-C12 alkyl, C2-C12 alkenyl, or C2-C12 alkynyl. In a further aspect, $R^1$ is an optionally substituted group selected from C1-C12 heteroalkyl, C2-C12 heteroalkenyl, or C2-C12 heteroalkynyl. In a further aspect, $R^1$ is an optionally substituted group selected from C3-C12 mono cyclic or bicyclic cycloalkyl, C3-C12, mono cyclic or bicyclic cycloalkenyl, 3-12 membered monocyclic or bicyclic saturated or partially unsaturated heterocyclyl, phenyl, 8-10 membered aryl, or 5-6 membered heteroaryl having 1-4 heteroatoms independently selected from nitrogen, oxygen, or sulfur.

In one aspect, $R^1$ is an optionally substituted organic residue comprising 1 to 12 carbons, including methyl, ethyl, propyl, butyl, pentyl, hexyl, heptyl, octyl, nonyl, decyl, undecyl, and dodecyl. In a further aspect, $R^1$ is an optionally substituted organic residue comprising 1 to 10 carbons, including methyl, ethyl, propyl, butyl, pentyl, hexyl, heptyl, octyl, nonyl, and decyl. In a further aspect, $R^1$ is an optionally substituted organic residue comprising 1 to 8 carbons, including methyl, ethyl, propyl, butyl, pentyl, hexyl, heptyl, and octyl. In a further aspect, $R^1$ is an optionally substituted organic residue comprising 1 to 6 carbons, including methyl, ethyl, propyl, butyl, pentyl, and hexyl. In a further aspect, $R^1$ can be an optionally substituted organic residue comprising 1 to 4 carbons, including methyl, ethyl, propyl, and butyl.

In a further aspect, $R^1$ is selected from optionally substituted C1-C12 alkyl or C2-C12 alkenyl or C2-C12 alkynyl, optionally substituted C1-C12 heteroalkyl or C2-C12 heteroalkenyl or C2-C12 heteroalkynyl, optionally substituted C3-C12 cycloalkyl or C3-C12 cycloalkenyl, optionally substituted C3-C12 heterocycloalkyl or C3-C12 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, and alkylamine-carbonyl.

c. $R^2$ Groups

In one aspect, each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons. In a further aspect, each $R^2$ is independently hydrogen or optionally substituted organic residue comprising from 1 to 6 carbons.

In a further aspect, $R^{2a}$ and $R^{2b}$ are independently optionally substituted organic residue comprising 1 to 6 carbons, including methyl, ethyl, propyl, butyl, pentyl, and hexyl. In a further aspect, each $R^2$ can be an optionally substituted organic residue comprising 1 to 4 carbons, including methyl, ethyl, propyl, and butyl. In a further aspect, both $R^{2a}$ and $R^{2b}$ are each two hydrogens.

In a further aspect, one of each $R^{2a}$ is hydrogen, while the other is optionally substituted organic residue comprising 1 to 6 carbons, for example 1 to 4 carbons. In a further aspect, one of each $R^{2b}$ is hydrogen, while the other is optionally substituted organic residue comprising 1 to 6 carbons, for example 1 to 4 carbons. In a further aspect, one of $R^{2a}$ and $R^{2b}$ is hydrogen, and the other of $R^{2a}$ and $R^{2b}$ is optionally substituted organic residue comprising 1 to 6 carbons, for example 1 to 4 carbons.

d. $R^3$ Groups

In one aspect, each of $R^{3a}$ and $R^{3b}$ are two substituents, oriented in a syn geometry relative to each other, independently selected from hydrogen and optionally substituted organic residue comprising 1 to 6 carbons. For example, $R^{3a}$ and $R^{3b}$ can be independently selected from optionally substituted C1-C6 alkyl, including methyl, ethyl, propyl, butyl, pentyl, and hexyl. In a further aspect, $R^3$ can be an optionally substituted organic residue comprising 1 to 4 carbons, including methyl, ethyl, propyl, and butyl.

In a further aspect, both $R^{3a}$ and $R^{3b}$ are hydrogen. In a further aspect, each $R^3$ can be an optionally substituted organic residue comprising 1 to 4 carbons, including methyl, ethyl, propyl, and butyl. In a further aspect, both $R^{3a}$ and $R^{3b}$ are hydrogen. In a further aspect, one of $R^{3a}$ and $R^{3b}$ is hydrogen, and the other of $R^{3a}$ and $R^{3b}$ is optionally substituted organic residue comprising 1 to 6 carbons, for example 1 to 4 carbons.

In a further aspect, all of $R^{2a}$, $R^{2b}$, $R^{3a}$, and $R^{3b}$ are hydrogen. In a further aspect, one of $R^{2a}$, $R^{2b}$, $R^{3a}$, and $R^{3b}$ is optionally substituted C1-C6 alkyl, for example optionally substituted C1-C4 alkyl, and the remaining of $R^{2a}$, $R^{2b}$, $R^{3a}$, and $R^{3b}$ are hydrogen e. $R^4$ Groups In one aspect, $R^4$ is selected from hydrogen, halogen, OR, cyano, nitro, SR, $N(R)_2$, and optionally substituted organic residue comprising 1 to 12 carbons.

In a further aspect, $R^4$ is selected from C1-C12 alkyl or C2-C12 alkenyl or C2-C12 alkynyl, optionally substituted C1-C12 heteroalkyl or C2-C12 heteroalkenyl or C2-C12 heteroalkynyl, optionally substituted C3-C12 cycloalkyl or C3-C12 cycloalkenyl, optionally substituted C3-C12 heterocycloalkyl or C3-C12 heterocycloalkenyl, optionally substituted aryl, optionally substituted heteroaryl. In one aspect, $R^4$ is optionally substituted monocyclic or bicyclic C3-C12 cycloalkyl.

In one aspect, $R^4$ is an optionally substituted organic residue comprising 1 to 12 carbons, including methyl, ethyl, propyl, butyl, pentyl, hexyl, heptyl, octyl, nonyl, decyl, undecyl, and dodecyl. In a further aspect, $R^4$ is an optionally substituted organic residue comprising 1 to 10 carbons, including methyl, ethyl, propyl, butyl, pentyl, hexyl, heptyl, octyl, nonyl, and decyl. In a further aspect, $R^4$ is an optionally substituted organic residue comprising 1 to 8 carbons, including methyl, ethyl, propyl, butyl, pentyl, hexyl, heptyl, and octyl. In a further aspect, $R^4$ is an optionally substituted organic residue comprising 1 to 6 carbons, including methyl, ethyl, propyl, butyl, pentyl, and hexyl. In a further aspect, $R^4$ can be an optionally substituted organic residue comprising 1 to 4 carbons, including methyl, ethyl, propyl, and butyl.

f. $R^5$ Groups

In one aspect, $R^5$ comprises two substituents independently selected from hydrogen, halogen, OR, cyano, nitro, SR, $N(R)_2$, and optionally substituted organic residue comprising 1 to 6 carbons. In a further aspect, each $R^5$ is independently selected from hydrogen, halogen, hydroxyl, nitrile, nitro, thiol, optionally substituted amino, and optionally substituted organic residue comprising from 1 to 6 carbons.

In a further aspect, $R^5$ is an optionally substituted organic residue comprising 1 to 6 carbons, including methyl, ethyl, propyl, butyl, pentyl, and hexyl. In a further aspect, $R^5$ can be an optionally substituted organic residue comprising 1 to 4 carbons, including methyl, ethyl, propyl, and butyl.

In a further aspect, both of the two $R^5$ substituents are hydrogen. In a further aspect, one of the two $R^5$ substituents is hydrogen. In a further aspect, one of the two $R^5$ substituents is hydrogen, and the other of the two $R^5$ substituents is selected from hydrogen, halogen, OR, cyano, nitro, SR, $N(R)_2$, and optionally substituted organic residue comprising 1 to 6 carbons. In a further aspect, the two $R^5$ substituents are different, thereby having a stereochemistry of R or S at the adjacent carbon.

g. $R^6$ Groups

In one aspect, $R^6$ comprises five substituents independently selected from hydrogen, halogen, OR, cyano, nitro SR, $N(R)_2$, and optionally substituted organic residue comprising from 1 to 6 carbon atoms.

For example, in some aspects, $R^6$ substituents can be present within a disclosed compound as represented by a formula:

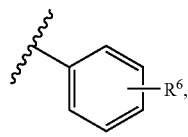

which, as stated above, is understood to be equivalent to a formula:

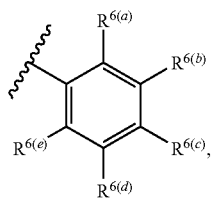

Thus, from 0 to 5 non-hydrogen (e.g., 0, 1, 2, 3, 4, or 5) substituents can be present. In a further aspect, each $R^6$ is independently selected from hydrogen, halogen, and optionally substituted organic residue comprising from 1 to 6 carbons.

In a further aspect, each $R^6$ is an optionally substituted organic residue comprising from 1 to 6 carbons. For example, each $R^6$ can be methyl, ethyl, propyl, butyl, pentyl, or hexyl. In a further aspect, each $R^6$ can be an optionally substituted organic residue comprising 1 to 4 carbons, including methyl, ethyl, propyl, and butyl. In a further aspect, each $R^6$ can be an optionally substituted organic residue comprising 1 to 2 carbons, including methyl, ethyl. In a further aspect, each $R^6$ can be an optionally substituted organic residue comprising 2 to 4 carbons, including ethyl, propyl, and butyl. In a further aspect, each $R^6$ can be an optionally substituted organic residue comprising 1 to 3 carbons, including methyl, ethyl, and propyl. In a further aspect, $R^6$ is substituted with 0-3 non-hydrogen groups selected from fluoro, chloro, bromo, hydroxyl, alkoxyl, nitrile, nitro, thiol, and optionally substituted amino. In a further aspect, $R^6$ is substituted with 1-2 non-hydrogen groups selected from fluoro, chloro, bromo, hydroxyl, alkoxyl, nitrile, nitro, thiol, and optionally substituted amino. In a further aspect, $R^6$ is substituted with 2 non-hydrogen groups selected from fluoro, chloro, bromo, hydroxyl, alkoxyl, nitrile, nitro, thiol, and optionally substituted amino. In a further aspect, $R^6$ is substituted with 1 non-hydrogen group selected from fluoro, chloro, bromo, hydroxyl, alkoxyl, nitrile, nitro, thiol, and optionally substituted amino.

h. $R^7$ Groups

In one aspect, $R^7$ is hydrogen or optionally substituted organic residue comprising from 1 to 9 carbons. In one aspect, $R^7$ is hydrogen. In one aspect, $R^7$ is optionally substituted organic residue comprising from 1 to 9 carbons. In a further aspect, $R^7$ is selected from methyl, ethyl, n-propyl, i-propyl, cyclopropyl, n-butyl, i-butyl, s-butyl, pentyl, hexyl, heptyl, octyl, nonyl, phenyl, and benzyl. In a further aspect, $R^7$ is an optionally substituted organic residue comprising 1 to 8 carbons, including methyl, ethyl, propyl, butyl, pentyl, hexyl, heptyl, and octyl. In a further aspect, $R^7$ is an optionally substituted organic residue comprising 1 to 6 carbons, including methyl, ethyl, propyl, butyl, pentyl, and hexyl. In a further aspect, $R^7$ can be an optionally substituted organic residue comprising 1 to 4 carbons, including methyl, ethyl, propyl, and butyl. In a further aspect, $R^7$ is methyl.

i. $R^8$ Groups

In one aspect, $R^8$ is an optionally substituted organic residue comprising 1 to 12 carbon atoms. In a further aspect, $R^8$ is an optionally substituted group selected from C1-C12 alkyl, C2-C12 alkenyl, or C2-C12 alkynyl. In a further aspect, $R^8$ is an optionally substituted group selected from C1-C12 heteroalkyl, C2-C12 heteroalkenyl, or C2-C12 heteroalkynyl. In a further aspect, $R^8$ is an optionally substituted group selected from C3-C12 mono cyclic or bicyclic cycloalkyl, C3-C12, mono cyclic or bicyclic cycloalkenyl, 3-12 membered monocyclic or bicyclic saturated or partially unsaturated heterocyclyl, phenyl, 8-10 membered aryl, or 5-6 membered heteroaryl having 1-4 heteroatoms independently selected from nitrogen, oxygen, or sulfur.

In one aspect, $R^8$ is an optionally substituted organic residue comprising 1 to 12 carbons, including methyl, ethyl, propyl, butyl, pentyl, hexyl, heptyl, octyl, nonyl, decyl, undecyl, and dodecyl. In a further aspect, $R^8$ is an optionally substituted organic residue comprising 1 to 10 carbons, including methyl, ethyl, propyl, butyl, pentyl, hexyl, heptyl, octyl, nonyl, and decyl. In a further aspect, $R^8$ is an optionally substituted organic residue comprising 1 to 8 carbons, including methyl, ethyl, propyl, butyl, pentyl, hexyl, heptyl, and octyl. In a further aspect, $R^8$ is an optionally substituted organic residue comprising 1 to 6 carbons, including methyl, ethyl, propyl, butyl, pentyl, and hexyl. In a further aspect, $R^8$ can be an optionally substituted organic residue comprising 1 to 4 carbons, including methyl, ethyl, propyl, and butyl.

In a further aspect, $R^8$ is selected from optionally substituted C1-C12 alkyl or C2-C12 alkenyl or C2-C12 alkynyl, optionally substituted C1-C12 heteroalkyl or C2-C12 heteroalkenyl or C2-C12 heteroalkynyl, optionally substituted C3-C12 cycloalkyl or C3-C12 cycloalkenyl, optionally substituted C3-C12 heterocycloalkyl or C3-C12 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, and alkylamine-carbonyl.

j. Example Compounds

In a further aspect, the compound is present as:

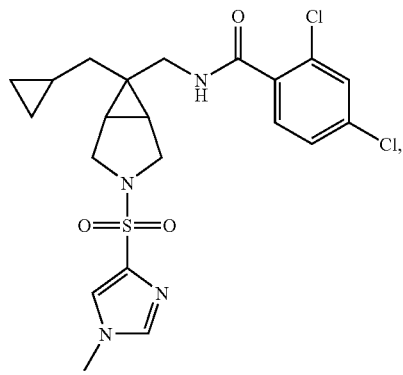

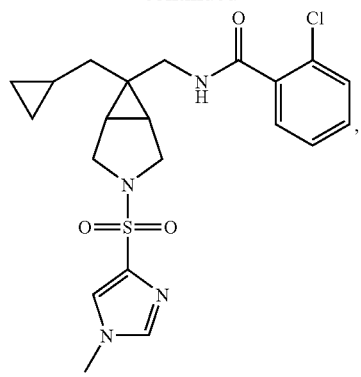
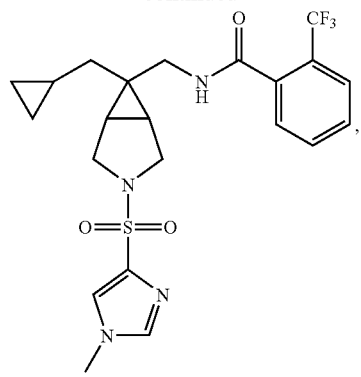
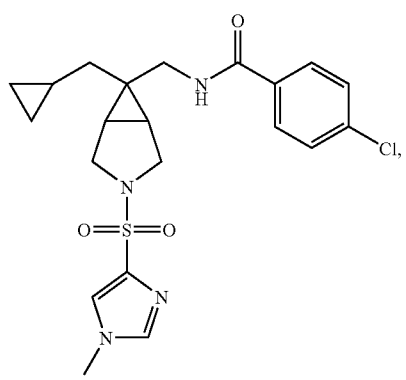
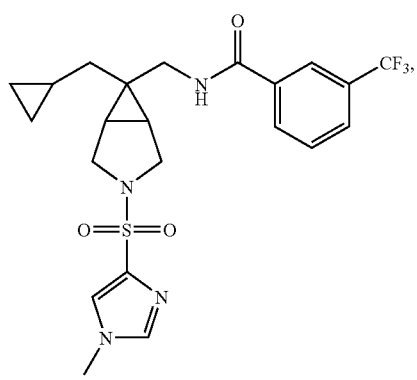
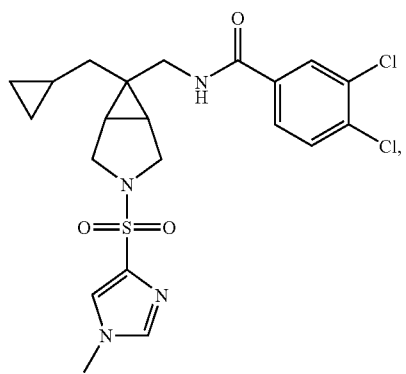
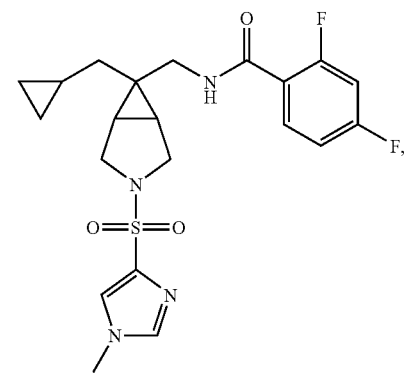
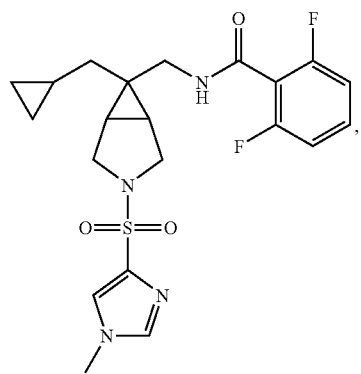
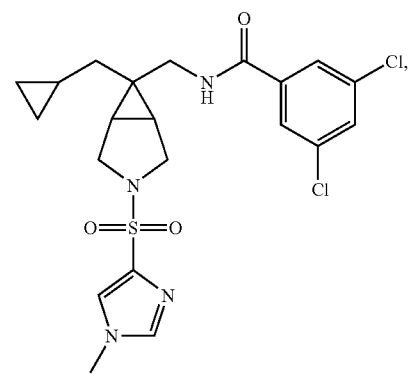

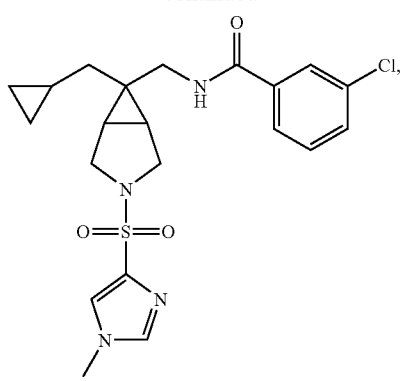
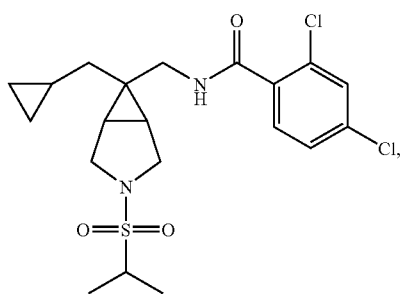
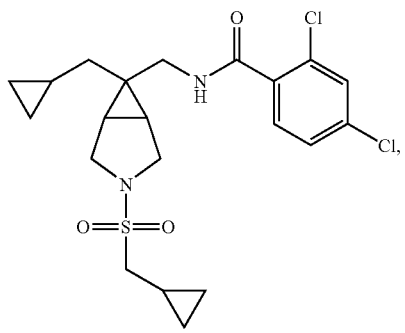
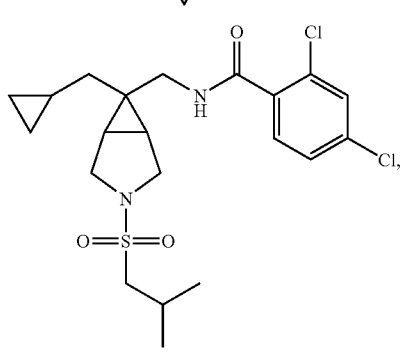
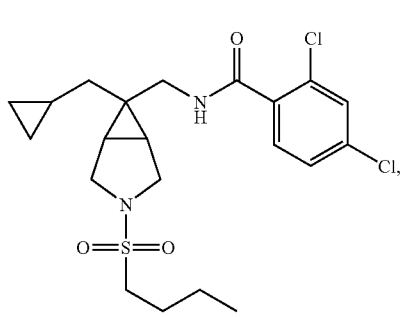
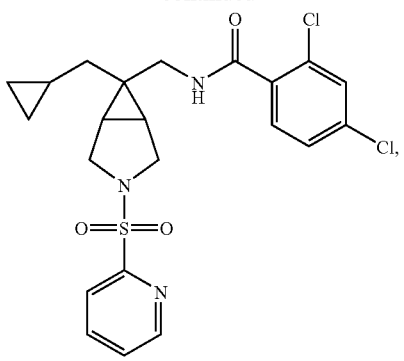
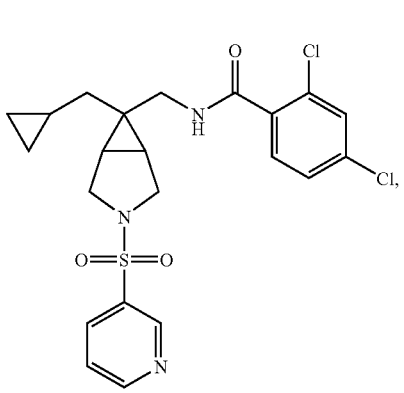
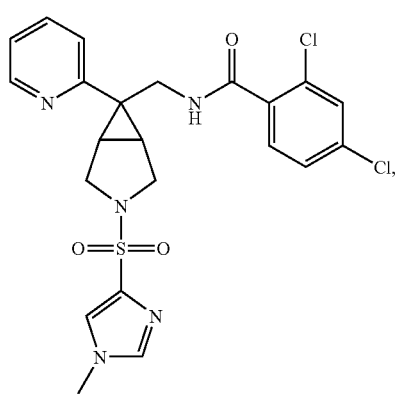
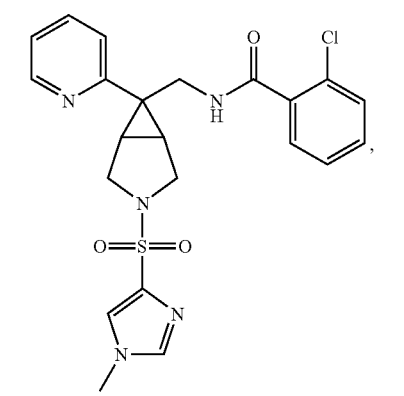

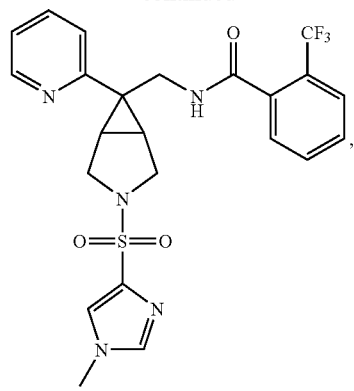
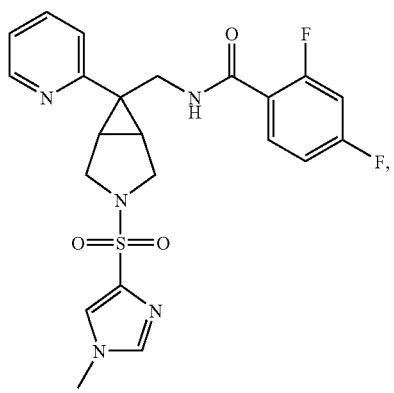
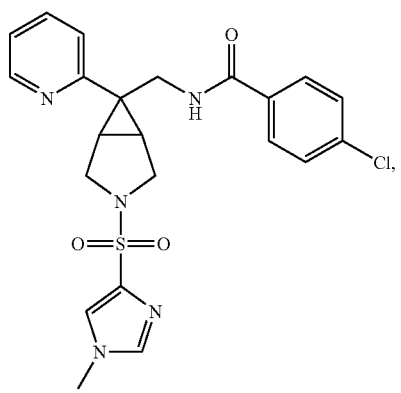
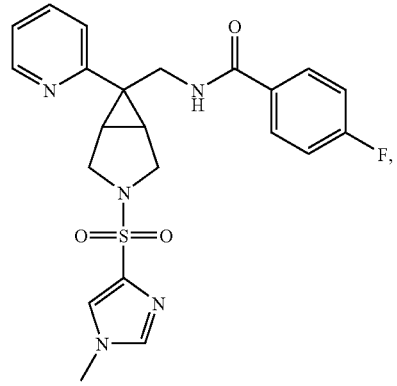
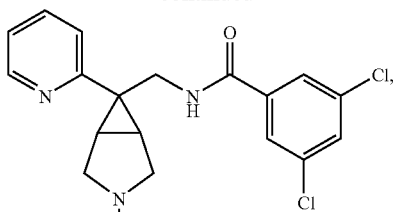
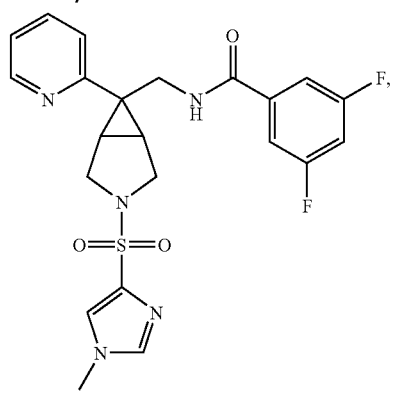
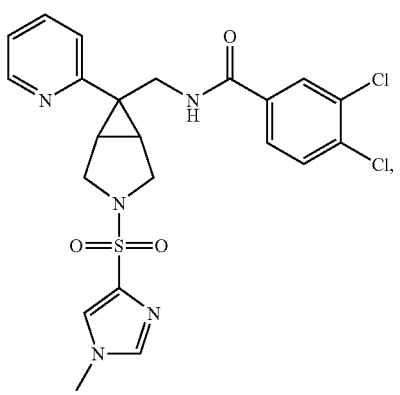
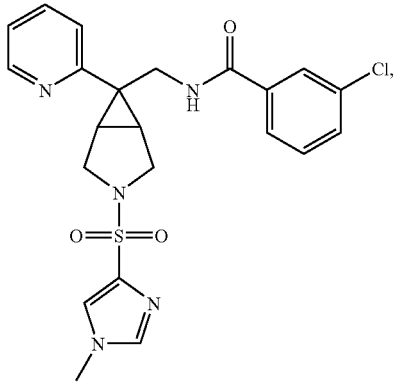

-continued
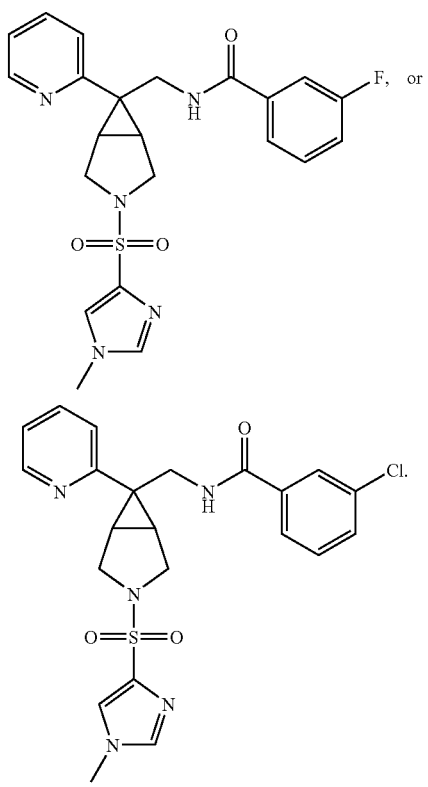
In a further aspect, the compound is present as:
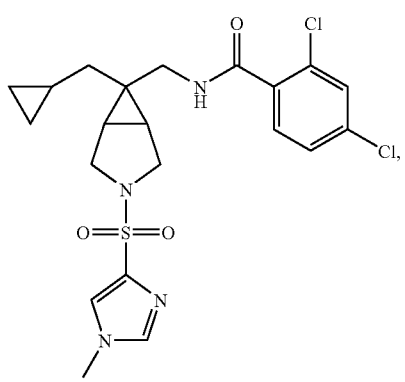
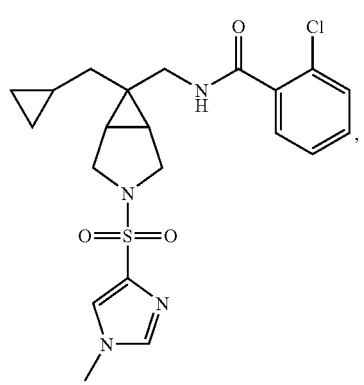
-continued
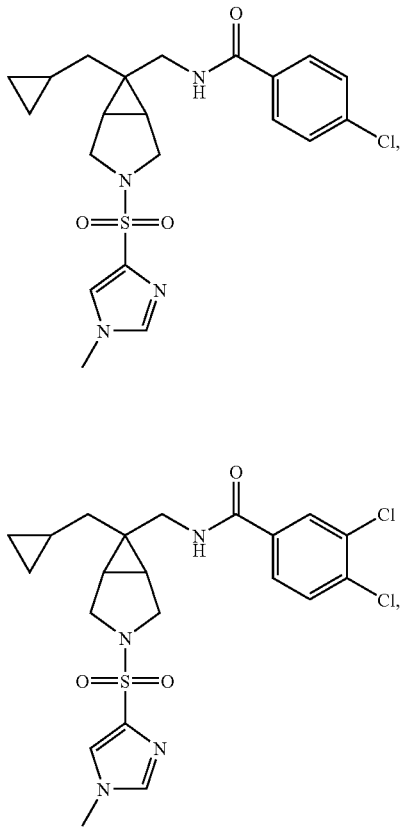
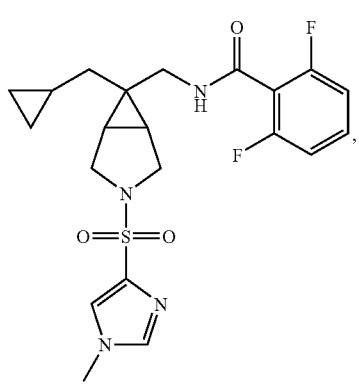
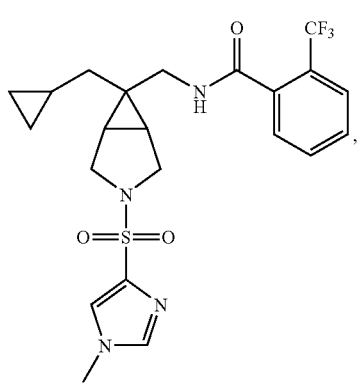

-continued
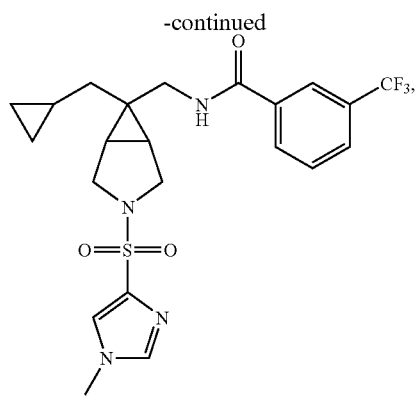
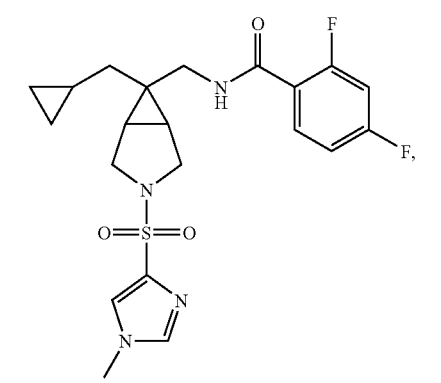
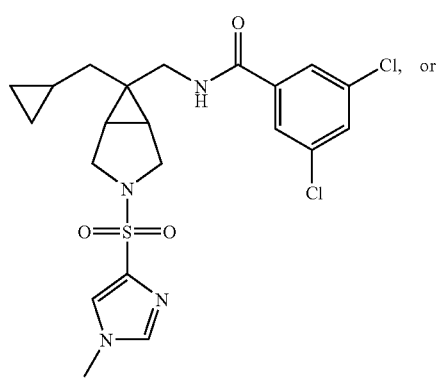 or
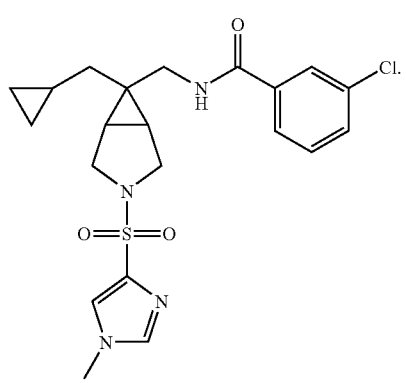
In a further aspect, the compound is present as:
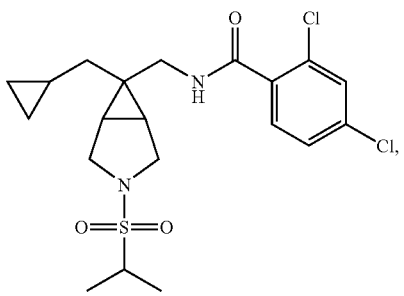
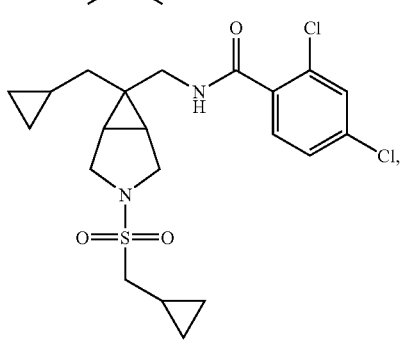
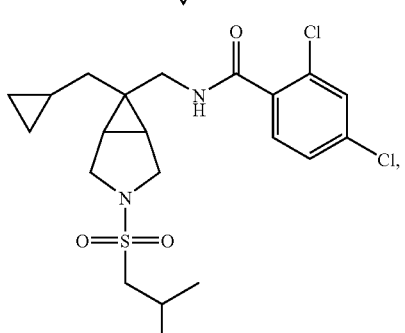
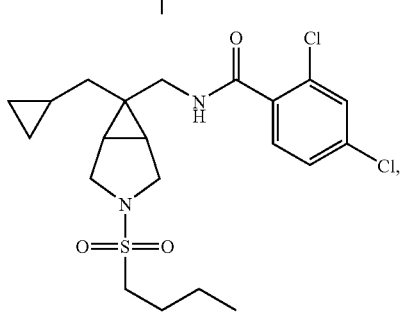
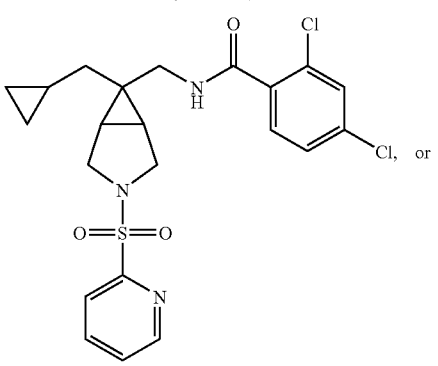 or

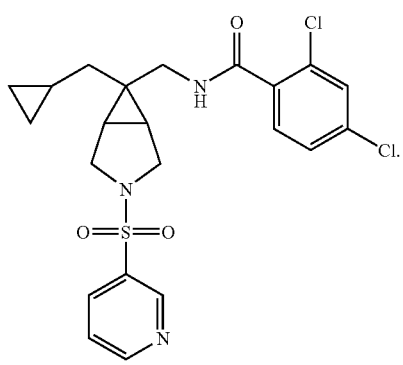 [SMILES: O=C(NCC1(CC2CC2)C2CN(S(=O)(=O)c3cccnc3)CC21)c1ccc(Cl)cc1Cl]
In a further aspect, the compound is present as:
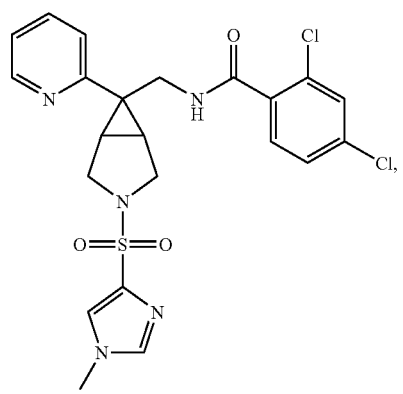
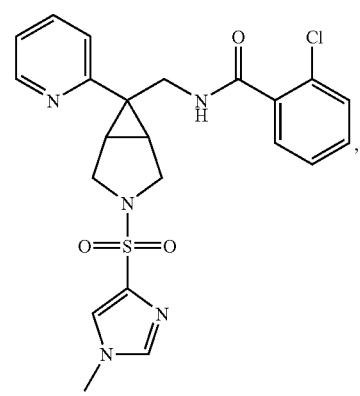
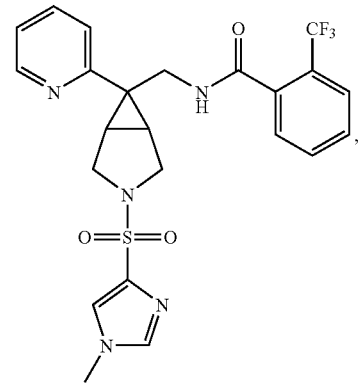
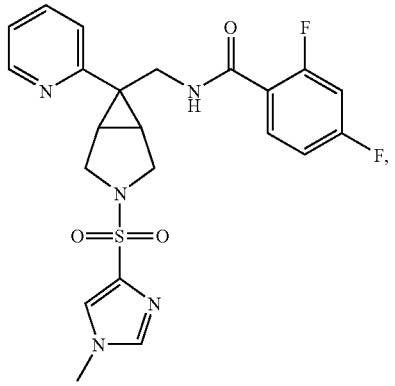
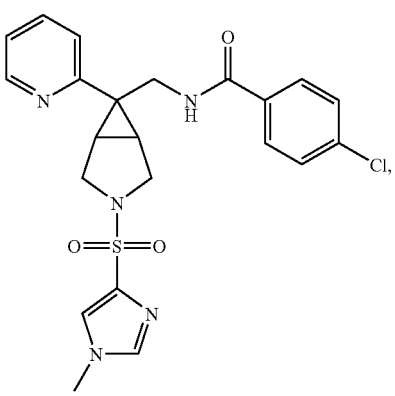
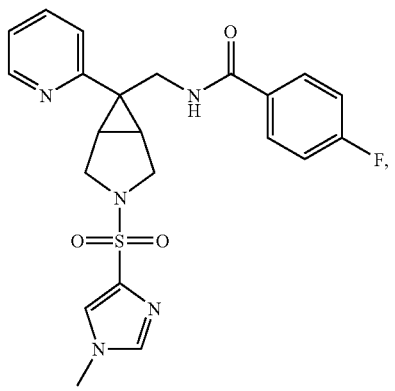
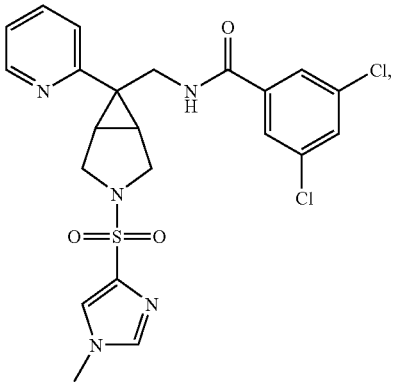

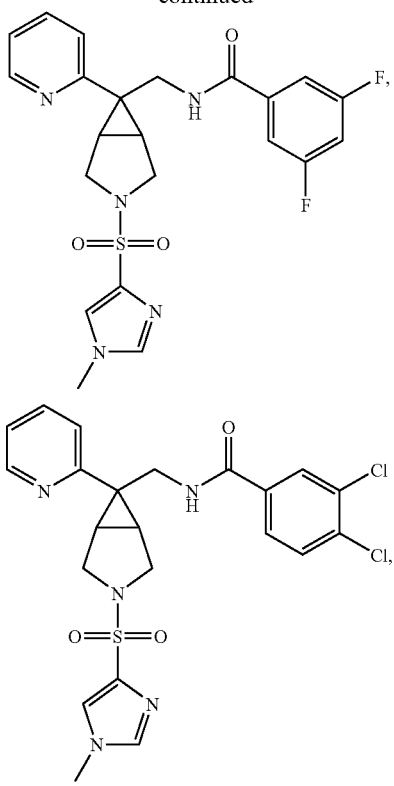

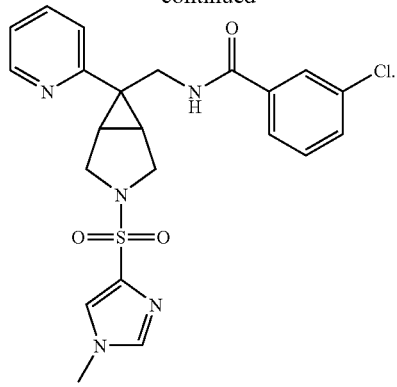

It is understood that the disclosed compounds can be used in connection with the disclosed methods, compositions, kits, and uses.

2. GlyT1 Activity

The utility of the compounds in accordance with the present invention as inhibitors of glycine type 1 transporter (GlyT1) activity can be demonstrated by methodology known in the art or by methods disclosed herein. As an example, GlyT1 activity can be demonstrated by known methods. Human placental choriocarcinoma cells endogenously expressing GlyT1 can be cultured using standard conditions. Cells can then be grown at 37° C. in a humidified atmosphere 40-48 hours before the assay. Culture medium can be removed from the culture plate, and cells can be incubated with an amount of TB1A buffer with or without the compounds of the present invention for a sufficient period of time. Then an amount of [$^{14}$C]-glycine diluted with TB1A can be added to each well. After incubation the microplates can be sealed and counted. Non-specific uptake of [$^{14}$C]-glycine can be determined in the presence of unlabeled glycine. To determine potencies, a range of concentrations of the compounds of the present invention can be added to the cells, followed by the fixed concentration of [$^{14}$C]-glycine. The concentration of the present compound that inhibited half of the specific uptake of [$^{14}$C]glycine (IC50 value) can be determined from the assay data by non-linear curve fitting.

In one aspect, the compound can have a GlyT1 inhibitory $IC_{50}$ of less than about 100 μM, for example, less than about 20 μM, 10 μM, 8 μM, or 5 μM. In a further aspect, the compound can have an $IC_{50}$ of less than about 1 μM. In a still further aspect, the compound can have an $IC_{50}$ of less than about 150 nM. In yet a further aspect, the compound can have a GlyT1 inhibitory $IC_{50}$ of from about 0 μM to about 10 μM, of from about 0 μM to about 8 μM, of from about 0 nM to about 150 nM.

C. METHODS OF MAKING THE COMPOUNDS

In one aspect, the invention relates to methods of making compounds useful as inhibitors of glycine type 1 transporter (GlyT1) activity, which can be useful in the treatment disorder associated with glycine type 1 transporter (GlyT1) activity.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein. The disclosed transformations can, in various aspects, be accomplished with reactions and reagents therefor that are well known to those of skill in the art. Many of such reagents and reaction conditions are described by Richard C. Larock, COMPREHENSIVE ORGANIC TRANSFORMATIONS: A GUIDE TO FUNCTIONAL GROUP PREPARATIONS, 1999 John Wiley & Sons, Inc. It is contemplated that alternate reaction conditions can be employed.

In some aspects, disclosed compounds can be prepared according to general Scheme 1, below.

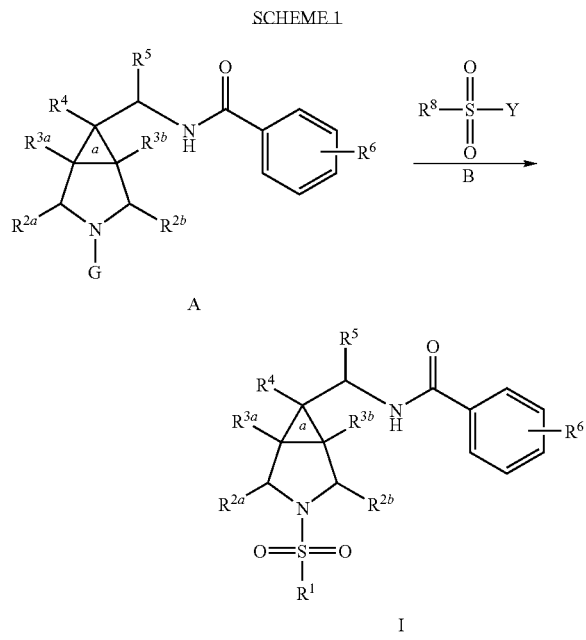

In Scheme 1, above, the step of treating a compound of formula A with a compound of formula B is typically performed in the presence of a suitable base and, optionally, in a suitable solvent. In some aspects, the suitable base is an organic base. In certain aspects, the organic base is diisopropylethylamine. In some aspects, the suitable solvent is a non-polar aprotic solvent. In certain aspects, the solvent is a hydrocarbon or halogenated hydrocarbon. In one aspect, group G is hydrogen. In some aspects, the suitable solvent is dichloromethane.

In certain aspects, disclosed compounds can be prepared according to general Scheme 2, below.

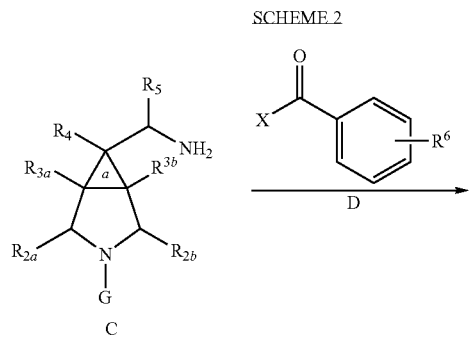

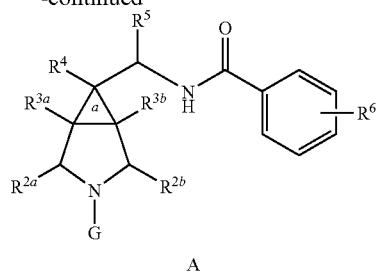

In Scheme 2, above, the step of treating a compound of formula C with a compound of formula D is performed in the presence of a suitable base and, optionally, in a suitable solvent. In some aspects, the suitable base is an organic base. In certain aspects, the organic base is diisopropylethylamine. In some aspects, the suitable solvent is a non-polar aprotic solvent. In certain aspects, the solvent is a hydrocarbon or halogenated hydrocarbon. In some aspects, the suitable solvent is dichloromethane. In one aspect, group G is a suitable amine protecting group.

In some aspects, the present invention provides a method according to Scheme 2, above, further comprising the step of treating the compound of formula A, after deprotection of the amine, with a compound of formula B to form a compound of formula I.

In a further aspect, group G is a residue of a compound of formula B. In such aspects, disclosed compounds can be prepared according to general Scheme 3, below.

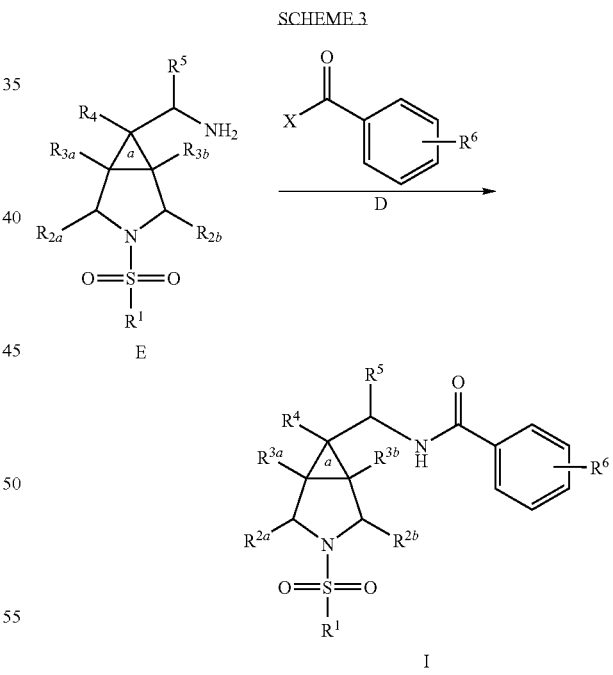

In Scheme 3, above, the step of treating a compound of formula E with a compound of formula D is performed in the presence of a suitable base and, optionally, in a suitable solvent. In some aspects, the suitable base is an organic base. In certain aspects, the organic base is diisopropylethylamine. In some aspects, the suitable solvent is a non-polar aprotic solvent. In certain aspects, the solvent is a hydrocarbon or halogenated hydrocarbon. In some aspects, the suitable solvent is dichloromethane.

Thus, in one aspect, the invention relates to methods for preparing a compound comprising the step of reacting a first compound or derivative thereof having a structure represented by a formula:

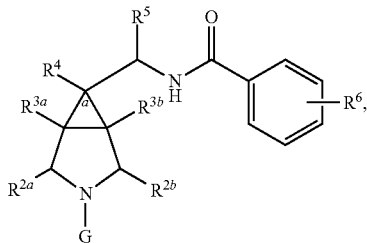

wherein each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, $N(R)_2$, and optionally substituted organic residue comprising 1 to 12 carbons; wherein $R^5$ comprises two substituents independently selected from hydrogen, halogen, OR, cyano, nitro, SR, $N(R)_2$, and optionally substituted organic residue comprising 1 to 6 carbons; wherein $R^6$ comprises five substituents independently selected from hydrogen, halogen, OR, cyano, nitro SR, $N(R)_2$, and optionally substituted organic residue comprising from 1 to 6 carbon atoms; wherein G is hydrogen or a protecting group; with a second compound having a structure represented by a formula:

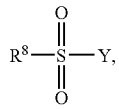

wherein $R^8$ is an optionally substituted organic residue comprising 1 to 12 carbon atoms; and wherein Y is a leaving group.

In a further aspect, the method comprises the steps of reacting a first compound or derivative thereof having a structure represented by a formula:

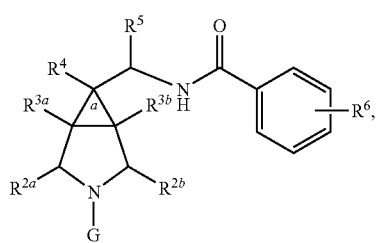

wherein each $R^{2a}$ and $R^{2b}$ comprises two substituents independently selected from hydrogen, halogen, hydroxyl, nitrile, nitro, thiol, optionally substituted amino, and optionally substituted organic residue comprising from 1 to 6 carbons; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, hydroxyl, cyano, nitro, thiol, amino, and optionally substituted organic residue comprising 1 to 12 carbons; wherein $R^5$ comprises two substituents independently selected from hydrogen, halogen, hydroxyl, cyano, nitro, thiol, amino, and optionally substituted organic residue comprising 1 to 6 carbons; wherein $R^6$ comprises five substituents independently selected from hydrogen, halogen, hydroxyl, cyano, nitro, thiol, amino, and optionally substituted organic residue comprising from 1 to 6 carbon atoms; wherein G is hydrogen or a protecting group; with a second compound having a structure represented by a formula:

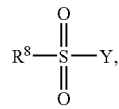

wherein $R^8$ is an optionally substituted organic residue comprising 1 to 12 carbon atoms; and wherein Y is a leaving group. In one aspect, Y is a halogen. In a further aspect, the carbon at position "a" has a stereochemistry of R or S.

In one aspect, the invention relates to methods for preparing a compound comprising the step of reacting a first compound or derivative thereof having a structure represented by a formula:

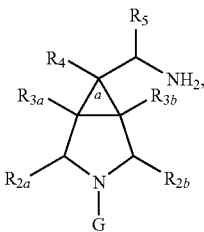

wherein each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, $N(R)_2$, and optionally substituted organic residue comprising 1 to 12 carbons; wherein $R^5$ comprises two substituents independently selected from hydrogen, halogen, OR, cyano, nitro, SR, $N(R)_2$, and optionally substituted organic residue comprising 1 to 6 carbons; wherein G is hydrogen, a protecting group, or a structure represented by a formula:

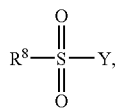

wherein $R^8$ is an optionally substituted organic residue comprising 1 to 12 carbon atoms; with a second compound, or synthetic equivalent thereof, having a structure represented by a formula:

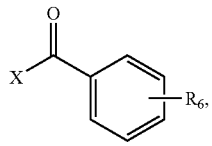

wherein $R^6$ comprises five substituents independently selected from hydrogen, halogen, OR, cyano, nitro SR, N(R)$_2$, and optionally substituted organic residue comprising from 1 to 6 carbon atoms; and wherein X is a leaving group.

In a further aspect, the method comprises the step of reacting a first compound or derivative thereof having a structure represented by a formula:

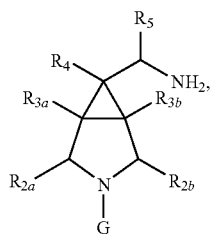

wherein each $R^{2a}$ and $R^{2b}$ comprises two substituents independently selected from hydrogen, halogen, hydroxyl, nitrile, nitro, thiol, optionally substituted amino, and optionally substituted organic residue comprising from 1 to 6 carbons; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, hydroxyl, cyano, nitro, thiol, amino, and optionally substituted organic residue comprising 1 to 12 carbons; wherein $R^5$ comprises two substituents independently selected from hydrogen, halogen, hydroxyl, cyano, nitro, thiol, amino, and optionally substituted organic residue comprising 1 to 6 carbons; wherein G is hydrogen, a protecting group, or a structure represented by a formula:

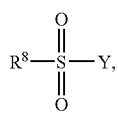

wherein $R^8$ is an optionally substituted organic residue comprising 1 to 12 carbon atoms; with a second compound, or synthetic equivalent thereof, having a structure represented by a formula:

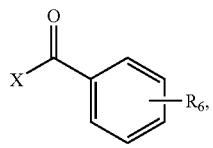

wherein $R^6$ comprises five substituents independently selected from hydrogen, halogen, hydroxyl, cyano, nitro, thiol, amino, and optionally substituted organic residue comprising from 1 to 6 carbon atoms; and wherein X is a leaving group. In one aspect, G is a hydrogen or a protecting group. In one aspect, G is a structure represented by a formula:

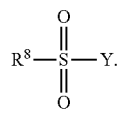

In a further aspect, X is a halogen. In a further aspect, the carbon at position "a" has a stereochemistry of R or S.

In one aspect, $R^1$ is selected from optionally substituted C1-C12 alkyl or C2-C12 alkenyl or C2-C12 alkynyl, optionally substituted C1-C12 heteroalkyl or C2-C12 heteroalkenyl or C2-C12 heteroalkynyl, optionally substituted C3-C12 cycloalkyl or C3-C12 cycloalkenyl, optionally substituted C3-C12 heterocycloalkyl or C3-C12 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, aminocarbonyl, and alkylamine-carbonyl.

In one aspect, $R^{2a}$ and $R^{2b}$ are independently selected from hydrogen and optionally substituted organic residue comprising from 1 to 6 carbons. In one aspect, both $R^{2a}$ and $R^{2b}$ are hydrogen. In one aspect, both $R^{3a}$ and $R^{3b}$ are hydrogen.

In one aspect, $R^4$ is selected from C1-C12 alkyl or C2-C12 alkenyl or C2-C12 alkynyl, optionally substituted C1-C12 heteroalkyl or C2-C12 heteroalkenyl or C2-C12 heteroalkynyl, optionally substituted C3-C12 cycloalkyl or C3-C12 cycloalkenyl, optionally substituted C3-C12 heterocycloalkyl or C3-C12 heterocycloalkenyl, optionally substituted aryl, optionally substituted heteroaryl.

In one aspect, each $R^5$ is hydrogen.

In one aspect, each $R^6$ is independently selected from hydrogen, halogen, and optionally substituted organic residue comprising from 1 to 6 carbons.

In one aspect, the resultant compound inhibits GlyT1 receptor response to glycine as a decrease in response to non-maximal concentrations of glycine in JAR cells in the presence of the compound, compared to the response of equivalent JAR cells to glycine in the absence of the compound, having an IC$_{50}$ of less than about 100 µM, for example, less than about 1 µM.

It is understood that the disclosed methods can be used in connection with the disclosed compounds, compositions, kits, and uses.

D. PHARMACEUTICAL COMPOSITIONS

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable derivatives (e.g., salt(s)) thereof) as an active ingredient, a pharmaceutically acceptable carrier, and, optionally, other therapeutic ingredients or adjuvants. The compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

The compounds of the present invention can be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable derivatives thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment of conditions which require inhibition of glycine transporter GlyT1 activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The disclosed pharmaceutical compositions can further comprise other therapeutically active compounds, as discussed further herein, which are usually applied in the treatment of the above mentioned pathological conditions.

It is understood that the disclosed compositions can be prepared from the disclosed compounds. It is also understood that the disclosed compositions can be employed in the disclosed methods of using.

E. METHODS OF USING THE COMPOUNDS AND COMPOSITIONS

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

In one aspect, the compounds can be coadministered with anti-Alzheimer's agents, beta-secretase inhibitors, gamma-secretase inhibitors, muscarinic agonists, muscarinic potentiators HMG-CoA reductase inhibitors, NSAIDs and anti-amyloid antibodies. In a further aspect, the compounds can be administered in combination with sedatives, hypnotics, anxiolytics, antipsychotics, selective serotonin reuptake inhibitors (SSRIs), monoamine oxidase inhibitors (MAOIs), 5-HT2 antagonists, GlyT1 inhibitors and the like such as, but not limited to: risperidone, clozapine, haloperidol, fluoxetine, prazepam, xanomeline, lithium, phenobarbitol, and salts thereof and combinations thereof.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders associated with glycine type 1 transporter (GlyT1) activity. Thus, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders associated with glycine type 1 transporter (GlyT1) activity in a subject comprising the step of administering to the subject at least one disclosed compound; at least one disclosed pharmaceutical composition; and/or at least one disclosed product in a dosage and amount effective to treat the disorder in the subject.

In one aspect, provided is a method for treating or preventing anxiety, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool for disorders including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

Also provided is a method for the treatment of a disorder in a mammal comprising the step of administering to the mammal at least one disclosed compound, composition, or medicament.

In one aspect, the NMDA receptor is central to a wide range of CNS processes, and plays a role in a variety of disease states in humans or other species. The action of GlyT1 transporters affects the local concentration of glycine around NMDA receptors. Selective GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Because a certain amount of glycine is needed for the efficient functioning of NMDA receptors, any change to that local concentration can affect NMDA-mediated neurotransmission. Changes in NMDA-mediated neurotransmission have been implicated in certain neuropsychiatric disorders such as dementia, depression and psychoses, for example schizophrenia, and learning and memory disorders, for example attention deficit disorders and autism.

In one aspect, the compounds of the present invention have utility in treating a variety of neurological and psychiatric disorders associated with glutamatergic neurotransmission dysfunction, including one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; NMDA receptor-related disorders such as autism, depression, benign forgetfulness, childhood learning disorders and closed head injury; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

In a specific aspect, the present invention provides a method for treating cognitive disorders, comprising: administering to a patient in need thereof an effective amount of a compound of the present invention. Particular cognitive disorders are dementia, delirium, amnestic disorders and age-related cognitive decline. At present, the text revision of the fourth edition of the Diagnostic and Statistical Manual of Mental Disorders (DSM-W-TR) (2000, American Psychiatric Association, Washington D. C.) provides a diagnostic tool that includes cognitive disorders including dementia, delirium, amnestic disorders and age-related cognitive decline. As used herein, the term "cognitive disorders" includes treatment of those mental disorders as described in DSM-W-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources. In another specific aspect, the present invention provides a method for treating anxiety disorders, comprising: administering to a patient in need thereof an effective amount of a compound of the present invention. Particular anxiety disorders are generalized anxiety disorder, obsessive-compulsive disorder and panic attack. At present, the text revision of the fourth edition of the Diagnostic and Statistical Manual of Mental Disorders (DSM-IV-TR) (2000, American Psychiatric Association, Washington D. C.) provides a diagnostic tool that includes anxiety disorders are generalized anxiety disorder, obsessive-compulsive disorder and panic attack. As used herein, the term "anxiety disorders" includes treatment of those mental disorders as described in DSM-W-TR. The skilled artisan will recognize that there are alternative nomenclatures, nosologies and classification systems for mental disorders, and that these systems evolve with medical and scientific progress. Thus the term "anxiety disorders" is intended to include like disorders that are described in other diagnostic sources.

In a further specific aspect, the present invention provides a method for treating schizophrenia or psychosis comprising: administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D. C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-W-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In a further specific aspect, the present invention provides a method for treating substance-related disorders and addictive behaviors, comprising: administering to a patient in need thereof an effective amount of a compound of the present invention. Particular substance-related disorders and addictive behaviors are persisting dementia, persisting amnestic disorder, psychotic disorder or anxiety disorder induced by substance abuse; and tolerance of, dependence on or withdrawal from substances of abuse. At present, the text revision of the fourth edition of the Diagnostic and Statistical Manual of Mental Disorders (DSM-IV-TR) (2000, American Psychiatric Association, Washington D. C.) provides a diagnostic tool that includes persisting dementia, persisting amnestic disorder, psychotic disorder or anxiety disorder induced by substance abuse; and tolerance of, dependence on or withdrawal from substances of abuse. As used herein, the term "substance-related disorders and addictive behaviors" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "substance-related disorders and addictive behaviors" is intended to include like disorders that are described in other diagnostic sources.

In a still further aspect, the present invention provides a method for treating pain, comprising: administering to a patient in need thereof an effective amount of a compound of the present invention. Particular pain aspects are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In a further aspect, the present invention provides a method for treating obesity or eating disorders associated with excessive food intake and complications associated therewith, comprising: administering to a patient in need thereof an effective amount of a compound of the present invention. At present, obesity is included in the tenth edition of the International Classification of Diseases and Related Health Problems (ICD-10) (1992 World Health Organization) as a general medical condition. The text revision of the fourth edition of the Diagnostic and Statistical Manual of Mental Disorders (DSM-IV-TR) (2000, American Psychiatric Association, Washington D. C.) provides a diagnostic tool that includes obesity in the presence of psychological factors affecting medical condition. As used herein, the term "obesity or eating disorders associated with excessive food intake" includes treatment of those medical conditions and disorders described in ICD-10 and DSM-W-TR. The skilled artisan will recognize that there are alternative nomenclatures, nosologies and classification systems for general medical conditions, and that these systems evolve with medical and scientific progress. Thus the term "obesity or eating disorders associated with excessive food intake" is intended to include like conditions and disorders that are described in other diagnostic sources.

The compounds are further useful in a method for the prevention, treatment, control, amelioration, or reducation of risk of the diseases, disorders and conditions noted herein.

The compounds are further useful in a method for the prevention, treatment, control, amelioration, or reduction of risk of the aforementioned diseases, disorders and conditions in combination with other agents, including an inhibitor of glycine transporter GlyT1 activity.

In one aspect, the compounds of the present invention can be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention include those that contain one or more other active ingredients, in addition to a compound of the present invention.

The above combinations include combinations of a disclosed compound not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient can be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be coadministered, either in concomitant therapy or in a fixed combination.

In one aspect, the compound can be employed in combination with anti-Alzheimer's agents, beta-secretase inhibitors, gamma-secretase inhibitors, HMG-CoA reductase inhibitors, NSADD's including ibuprofen, vitamin E, and anti-amyloid antibodies. In another aspect, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, Zolpidem, and salts thereof, and combinations thereof, and the like, or the subject compound may be administered in conjunction with the use of physical methods such as with light therapy or electrical stimulation.

In a further aspect, the compound can be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexol)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In a further aspect, the compound can be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In one aspect, the compound can be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HTJA agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In the treatment of conditions which require inhibition of glycine transporter GlyT1 activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15. 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to a method for inhibiting glyT1 activity in at least one cell comprising the step of contacting the at least one cell with at least one compound having a structure represented by a formula:

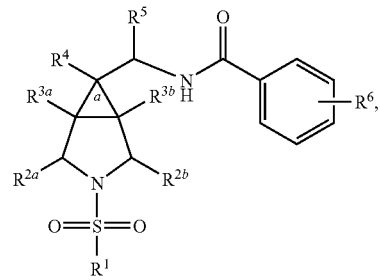

wherein $R^1$ is optionally substituted organic residue comprising 1 to 12 carbon atoms; wherein each $R^{2a}$ and $R^{2b}$ comprises two substituents independently selected from hydrogen, halogen, OR, nitrile, nitro, SR, N(R)$_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, N(R)$_2$, and optionally substituted organic residue comprising 1 to 12 carbons; wherein $R^5$ comprises two substituents independently selected from hydrogen, halogen, OR, cyano, nitro, SR, N(R)$_2$, and optionally substituted organic residue comprising 1 to 6 carbons; wherein $R^6$ comprises five substituents independently selected from hydrogen, halogen, OR, cyano, nitro SR, N(R)$_2$, and optionally substituted organic residue comprising from 1 to 6 carbon atoms; or a pharmaceutically acceptable derivative thereof, in an amount effective to inhibit glyT1 receptor activity in the at least one cell.

In a further aspect, the cell is mammalian, for example human. In a further aspect, the cell has been isolated from a subject prior to the contacting step. In a further aspect, contacting is via administration to a subject.

In one aspect, the invention relates to a method for inhibiting glyT1 activity in a subject comprising the step of administering to the subject a therapeutically effective amount of at least one compound having a structure represented by a formula:

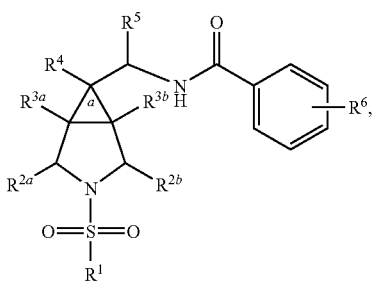

wherein $R^1$ is optionally substituted organic residue comprising 1 to 12 carbon atoms; wherein each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, $N(R)_2$, and optionally substituted organic residue comprising 1 to 12 carbons; wherein $R^5$ comprises two substituents independently selected from hydrogen, halogen, OR, cyano, nitro, SR, N$(R)_2$, and optionally substituted organic residue comprising 1 to 6 carbons; wherein $R^6$ comprises five substituents independently selected from hydrogen, halogen, OR, cyano, nitro SR, $N(R)_2$, and optionally substituted organic residue comprising from 1 to 6 carbon atoms; or a pharmaceutically acceptable derivative thereof, in a dosage and amount effective to inhibit glyT1 receptor activity in the subject.

In a further aspect, the subject is a mammal, for example a human. In a further aspect, the subject has been diagnosed with a need for treatment of the disorder prior to the administering step. In a further aspect, inhibiting glyT1 receptor activity in the subject comprises treatment of a disorder associated with cholinergic dysfunction in the subject.

In one aspect, the invention relates to a method for the treatment of a disorder associated with glycinergic or glutamatergic neurotransmission dysfunction in a mammal comprising the step of administering to the mammal at least one compound having a structure represented by a formula:

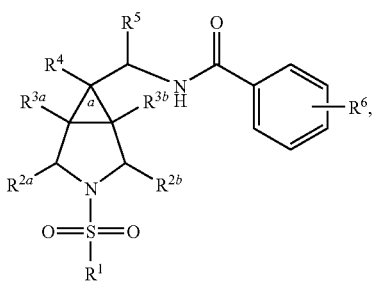

wherein $R^1$ is optionally substituted organic residue comprising 1 to 12 carbon atoms; wherein each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, $N(R)_2$, and optionally substituted organic residue comprising 1 to 12 carbons; wherein $R^5$ comprises two substituents independently selected from hydrogen, halogen, OR, cyano, nitro, SR, N$(R)_2$, and optionally substituted organic residue comprising 1 to 6 carbons; wherein $R^6$ comprises five substituents independently selected from hydrogen, halogen, OR, cyano, nitro SR, $N(R)_2$, and optionally substituted organic residue comprising from 1 to 6 carbon atoms; or a pharmaceutically acceptable derivative thereof, in a dosage and amount effective to treat the disorder in the mammal.

In a further aspect, the disorder is selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders. In a further aspect, the disorder is schizophrenia. In a further aspect, the disorder is a neurological and/or psychiatric disorder associated with glyT1 receptor activity dysfunction. In a further aspect, the disorder is a neurological or psychiatric disorder associated with glutamatergic neurotransmission dysfunction selected from: schizophrenia, psychosis, "schizophrenia-spectrum" disorders, depression, bipolar disorder, cognitive disorders, delirium, amnestic disorders, anxiety disorders, attention disorders, obesity, eating disorders, and NMDA receptor-related disorders.

In a further aspect, the mammal is a human. In a further aspect, the mammal has been diagnosed with a need for treatment of the disorder prior to the administering step. In a further aspect, the method further comprises the step of identifying a subject in need of glyT1 receptor activity inhibition.

It is understood that the disclosed methods can be used in connection with the disclosed compounds, compositions, kits, and uses.

2. Manufacture of a Medicament

The present invention is further directed to a method for the manufacture of a medicament for potentiating glutamate receptor activity (e.g., treatment of one or more neurological and/or psychiatric disorder associated with glutamate dysfunction) in mammals (e.g., humans) comprising combining one or more disclosed compounds, products, or compositions with a pharmaceutically acceptable carrier or diluent.

In one aspect, the invention relates to a method for the manufacture of a medicament for inhibition of glyT1 receptor activity in a mammal comprising combining at least one compound having a structure represented by a formula:

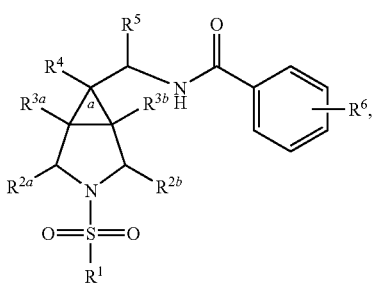

wherein $R^1$ is optionally substituted organic residue comprising 1 to 12 carbon atoms; wherein each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, $N(R)_2$, and optionally substituted organic residue comprising 1 to 12 carbons; wherein $R^5$ comprises two substituents independently selected from hydrogen, halogen, OR, cyano, nitro, SR, $N(R)_2$, and optionally substituted organic residue comprising 1 to 6 carbons; wherein $R^6$ comprises five substituents independently selected from hydrogen, halogen, OR, cyano, nitro SR, $N(R)_2$, and optionally substituted organic residue comprising from 1 to 6 carbon atoms; or a pharmaceutically acceptable derivative thereof, with a pharmaceutically acceptable carrier. In a further aspect, the carbon at position "a" has a stereochemistry of R or S.

In a further aspect, a medicament can comprise a compound having a structure represented by the formula:

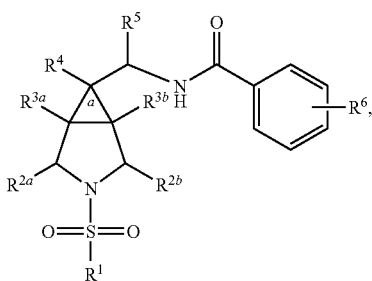

wherein $R^1$ is optionally substituted organic residue comprising 1 to 12 carbon atoms; wherein each $R^{2a}$ and $R^{2b}$ comprises two substituents independently selected from hydrogen, halogen, hydroxyl, nitrile, nitro, thiol, optionally substituted amino, and optionally substituted organic residue comprising from 1 to 6 carbons; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, hydroxyl, cyano, nitro, thiol, amino, and optionally substituted organic residue comprising 1 to 12 carbons; wherein $R^5$ comprises two substituents independently selected from hydrogen, halogen, hydroxyl, cyano, nitro, thiol, amino, and optionally substituted organic residue comprising 1 to 6 carbons; wherein $R^6$ comprises five substituents independently selected from hydrogen, halogen, hydroxyl, cyano, nitro, thiol, amino, and optionally substituted organic residue comprising 1 to 6 carbon atoms; or a pharmaceutically acceptable derivative thereof. In a further aspect, the carbon at position "a" has a stereochemistry of R or S.

In a further aspect, a medicament can comprise a product produced by a method comprising the step of reacting a first compound or derivative thereof having a structure represented by a formula:

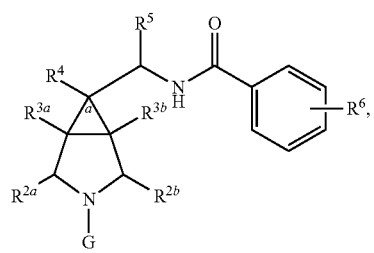

wherein each $R^{2a}$ and $R^{2b}$ comprises two substituents independently selected from hydrogen, halogen, hydroxyl, nitrile, nitro, thiol, optionally substituted amino, and optionally substituted organic residue comprising from 1 to 6 carbons; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, hydroxyl, cyano, nitro, thiol, amino, and optionally substituted organic residue comprising 1 to 12 carbons; wherein $R^5$ comprises two substituents independently selected from hydrogen, halogen, hydroxyl, cyano, nitro, thiol, amino, and optionally substituted organic residue comprising 1 to 6 carbons; wherein $R^6$ comprises five substituents independently selected from hydrogen, halogen, hydroxyl, cyano, nitro, thiol, amino, and optionally substituted organic residue comprising from 1 to 6 carbon atoms; wherein the carbon at position "a" has a stereochemistry of R or S; wherein G is hydrogen or a protecting group; with a second compound having a structure represented by a formula:

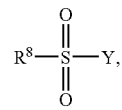

wherein $R^8$ is an optionally substituted organic residue comprising 1 to 12 carbon atoms; and wherein Y is a leaving group. In one aspect, Y is a halogen.

In a further aspect, a medicament can comprise a product produced by a method comprising the step of reacting a first compound or derivative thereof having a structure represented by a formula:

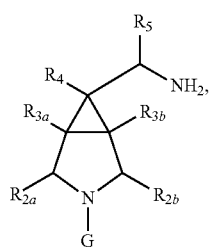

wherein each $R^{2a}$ and $R^{2b}$ comprises two substituents independently selected from hydrogen, halogen, hydroxyl, nitrile, nitro, thiol, optionally substituted amino, and optionally substituted organic residue comprising from 1 to 6 carbons; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, hydroxyl, cyano, nitro, thiol, amino, and optionally substituted organic residue comprising 1 to 12 carbons; wherein $R^5$ comprises two substituents independently selected from hydrogen, halogen, hydroxyl, cyano, nitro, thiol, amino, and optionally substituted organic residue comprising 1 to 6 carbons; wherein G is hydrogen, a protecting group, or a structure represented by a formula:

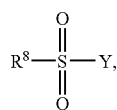

wherein $R^8$ is an optionally substituted organic residue comprising 1 to 12 carbon atoms; with a second compound, or synthetic equivalent thereof, having a structure represented by a formula:

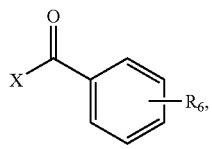

wherein $R^6$ comprises five substituents independently selected from hydrogen, halogen, hydroxyl, cyano, nitro, thiol, amino, and optionally substituted organic residue comprising from 1 to 6 carbon atoms; and wherein X is a leaving group. In one aspect, G is a hydrogen or a protecting group. In one aspect, G is a structure represented by a formula:

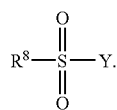

3. Use of Compounds

In one aspect, the invention relates to use of at least one compound having a structure represented by a formula:

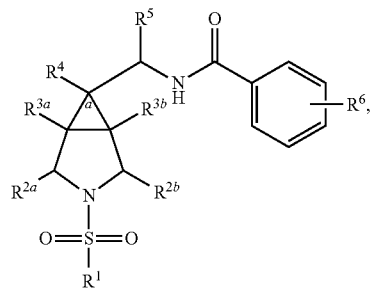

wherein $R^1$ is optionally substituted organic residue comprising 1 to 12 carbon atoms; wherein each $R^{2a}$ and $R^{2b}$ comprises two substituents independently selected from hydrogen, halogen, OR, nitrile, nitro, SR, N(R)$_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, N(R)$_2$, and optionally substituted organic residue comprising 1 to 12 carbons; wherein $R^5$ comprises two substituents independently selected from hydrogen, halogen, OR, cyano, nitro, SR, N(R)$_2$, and optionally substituted organic residue comprising 1 to 6 carbons; wherein $R^6$ comprises five substituents independently selected from hydrogen, halogen, OR, cyano, nitro SR, N(R)$_2$, and optionally substituted organic residue comprising from 1 to 6 carbon atoms; or a pharmaceutically acceptable derivative thereof, for inhibition of glyT1 receptor activity in a mammal.

In a further aspect, the mammal is a human. In a further aspect, the method further comprises the step of administration to a subject in need of glyT1 receptor activity inhibition. In a further aspect, the use comprises treatment of a disorder in a mammal. In a further aspect, the disorder is a neurological and/or psychiatric disorder associated with glyT1 receptor activity dysfunction.

Also provided is the use of a compound having a structure represented by the formula:

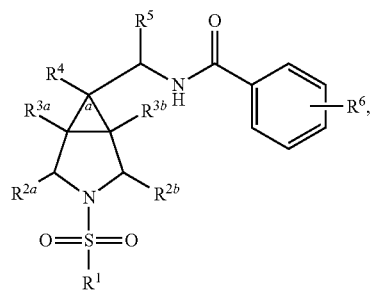

wherein $R^1$ is optionally substituted organic residue comprising 1 to 12 carbon atoms; wherein each $R^{2a}$ and $R^{2b}$ comprises two substituents independently selected from hydrogen, halogen, hydroxyl, nitrile, nitro, thiol, optionally substituted amino, and optionally substituted organic residue comprising from 1 to 6 carbons; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, hydroxyl, cyano, nitro, thiol, amino, and optionally substituted organic residue comprising 1 to 12 carbons; wherein $R^5$ comprises two substituents independently selected from hydrogen, halogen, hydroxyl, cyano, nitro, thiol, amino, and optionally substituted organic residue comprising 1 to 6 carbons; wherein $R^6$ comprises five substituents independently selected from hydrogen, halogen, hydroxyl, cyano, nitro, thiol, amino, and optionally substituted organic residue comprising from 1 to 6 carbon atoms; or a pharmaceutically acceptable derivative thereof.

In one aspect, the use relates to a treatment of a disorder in a mammal. In one aspect, the use is characterized in that the mammal is a human. In one aspect, the use is characterized in that the disorder is a disorder associated with glycine type 1 transporter (GlyT1) activity.

It is understood that the disclosed uses can be employed in connection with the disclosed compounds, methods, compositions, and kits.

4. Antagonism of GlyT1 Activity

Also provided is a method for inhibition of glycine type 1 transporter (GlyT1) activity in at least one cell comprising the step of contacting the at least one cell with at least one disclosed compound in an amount effective to inhibit GlyT1 receptor activity in the at least one cell. In a further aspect, provided is a method for inhibition of GlyT1 receptor activity in a subject comprising the step of administering to the subject a therapeutically effective amount of at least one disclosed compound, in a dosage and amount effective to inhibit GlyT1 receptor activity in the subject. In a further aspect, the method can be applied to a subject, e.g., a mammal, including, for example, a human.

5. Subjects

The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder treatable by inhibition of GlyT1 activity and/or or a need for inhibition of GlyT1 activity prior to the administering step. In some aspects of the disclosed method, the subject has been diagnosed with anxiety or a related disorder prior to the administering step. In some aspects of the disclosed methods, the subject has been identified with a need for treatment prior to the administering step. In some aspects of the disclosed method, the subject has been identified with a disorder treatable by inhibition of GlyT1 activity and/or or a need for inhibition of GlyT1 activity prior to the administering step. In some aspects of the disclosed method, the subject has been identified with anxiety or a related disorder prior to the administering step. In one aspect, a subject can be treated prophylactically with a compound or composition disclosed herein, as discussed herein elsewhere.

F. KITS

In one aspect, the invention relates to a kit comprising at least one compound having a structure represented by a formula:

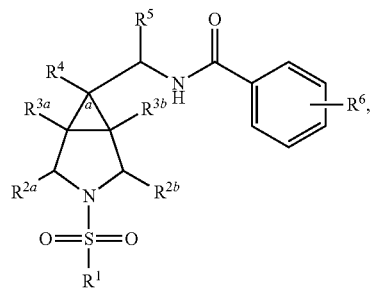

wherein $R^1$ is optionally substituted organic residue comprising 1 to 12 carbon atoms; wherein each $R^{2a}$ and $R^{2b}$ comprises two substituents independently selected from hydrogen, halogen, OR, nitrile, nitro, SR, $N(R)_2$, and optionally substituted organic residue comprising from 1 to 6 carbons; wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur; wherein $R^{3a}$ and $R^{3b}$ are two substituents oriented in a syn geometry relative to each other, wherein $R^{3a}$ and $R^{3b}$ are independently selected from hydrogen and optionally substituted organic residue comprising from 1 to 6 carbons; wherein $R^4$ is selected from hydrogen, halogen, OR, cyano, nitro, SR, $N(R)_2$, and optionally substituted organic residue comprising 1 to 12 carbons; wherein $R^5$ comprises two substituents independently selected from hydrogen, halogen, OR, cyano, nitro, SR, $N(R)_2$, and optionally substituted organic residue comprising 1 to 6 carbons; wherein $R^6$ comprises five substituents independently selected from hydrogen, halogen, OR, cyano, nitro SR, $N(R)_2$, and optionally substituted organic residue comprising from 1 to 6 carbon atoms; or a pharmaceutically acceptable derivative thereof, and one or more of: a. at least one agent known to increase glyT1 receptor activity; b. at least one agent known to decrease glyT1 receptor activity; c. at least one agent known to treat a glycinergic or glutamatergic neurotransmission dysfunction; or d. instructions for treating a disorder associated with glycinergic or glutamatergic neurotransmission dysfunction.

In a further aspect, the at least one compound and the at least one agent are co-formulated. In a further aspect, the at least one compound and the at least one agent are co-packaged.

It is understood that the disclosed kits can be prepared from the disclosed compounds, products, and pharmaceutical compositions. It is also understood that the disclosed kits can be employed in connection with the disclosed methods of using.

G. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. All $^1$H NMR spectra were obtained on instrumentation at a field strength of 300 to 500 MHz.

1. Synthesis of 3.1.0 Bicyclic GlyT1 Inhibitors

Compounds were prepared according to the following procedures:

a. General Procedure

The disclosed compounds and/or products can be synthesized according to the route shown below:

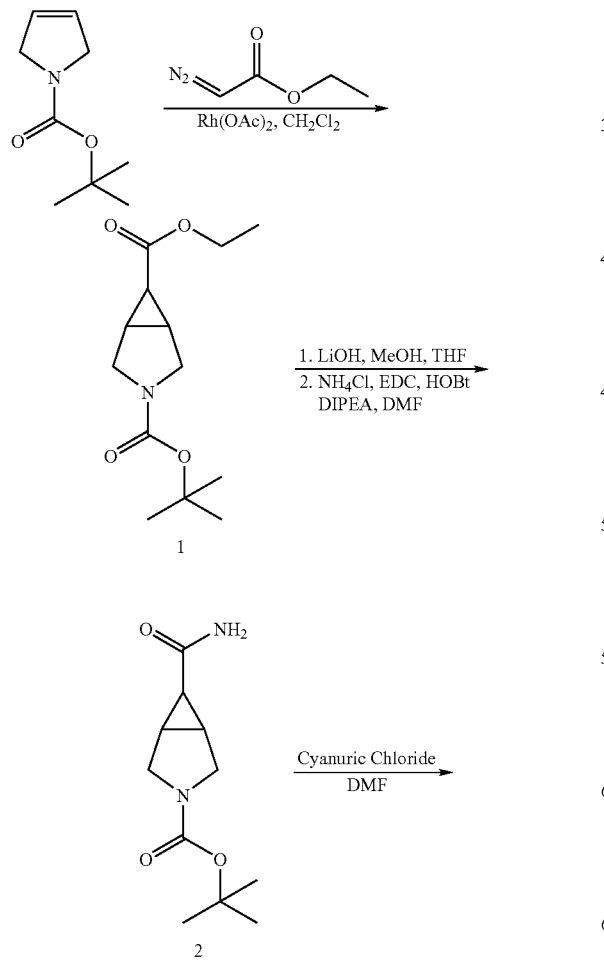

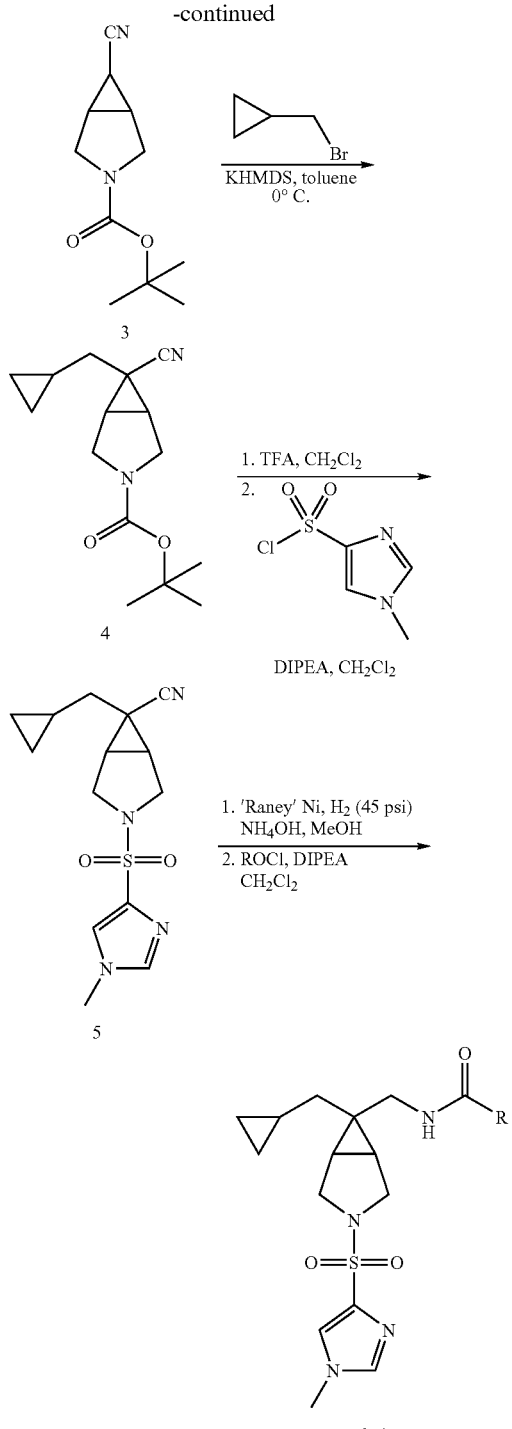

b. Synthesis of 3-tert-butyl 6-ethyl 3-azabicyclo[3.1.0] hexane-3,6-dicarboxylate, 1

To a solution of tert-butyl 2,5-dihydro-1H-pyrrole-1-carboxylate (10.0 g, 59.1 mmol) and Rh(OAc)$_2$ (500 mg) in CH$_2$Cl$_2$ (200 mL) was added a solution of ethyl diazoacetate (8.14 g, 71.5 mmol) in CH$_2$Cl$_2$ (80 mL) over 12 h with a syringe pump. The reaction was filtered through celite, concentrated under vacuum and purified by column chromatography (silica gel) using 0 to 45% EtOAc in hexanes to afford ester 1 (6.70 g, 44%) as a clear straw colored oil; $^1$H-nmr (400

MHz, CDCl₃) δ 4.18-4.03 (m, 2H), 3.71-3.53 (m, 2H), 3.39 (s, 2H), 2.04 (s, 2H), 1.42 (s, 9H), 1.28-1.19 (m, 3H).

c. Synthesis of 3-tert-butyl 6-carbamoyl-3-azabicyclo[3.1.0]hexane-3-carboxylate, 2

To a solution of 1 (6.65 g, 26.2 mmol) in THF (100 mL) and MeOH (40 mL) was added a solution of LiOH (4.40 g, 104 mmol) in H₂O (40 mL) and stirred for 2 h. The reaction was quenched upon addition of 0.5 N HCl (150 mL) and extracted with EtOAc (2×200 ml). The combined organic extracts were dried over MgSO₄ and concentrated under vacuum to afford the intermediate acid. Dissolved in DMF (90 mL), added DIPEA (18.8 mL, 104 mmol), EDC (5.84 g, 31.4 mmol), HOBt (4.24 g, 31.4 mmol) and NH₄Cl (4.16 g, 78.5 mmol). The reaction was sealed and stirred for 48 h. Diluted the reaction with water (350 mL) and extracted with EtOAc (2×250 mL). The combined organic extracts were washed with water (2×300 mL), brine (300 mL), dried over MgSO₄ and concentrated under vacuum to afford 2 (1.84 g, 31%) as a white solid; ¹H-nmr (400 MHz, CDCl₃) δ 5.75 (s, 1H), 5.45 (s, 1H), 3.68 (d, J=7.0 Hz, 1H), 3.58 (d, J=11.0 Hz, 1H), 3.43 (d, J=11.0 Hz, 2H), 2.07 (s, 2H), 1.44 (s, 9H), 1.31-1.26 (m, 1H); LC-MS (214 nM) 2.15 min (>98%), m/z 171 [M-tBu].

d. Synthesis of 3-tert-butyl 6-cyano-3-azabicyclo[3.1.0]hexane-3-carboxylate, 3

To a solution of 2 (1.83 g, 8.09 mmol) in DMF (30 mL) was added cyanuric chloride (1.50 g, 8.09 mmol) and stirred for 2 h. The reaction was diluted with water (100 mL) and extracted with EtOAc (2×80 mL). The combined organic extracts were washed with water (2×100 mL), brine (120 mL), dried over MgSO₄ and concentrated under vacuum to afford 3 (1.67 g, 99%) as a clear yellow oil; ¹H-nmr (400 MHz, CDCl₃) δ 3.80-3.58 (m, 2H), 3.40 (d, J=12.0 Hz, 2H), 2.16 (s, 2H), 1.43 (s, 9H), 1.25 (t, J=3.0 Hz, 1H).

e. Synthesis of 3-tert-butyl 6-cyano-6-(cyclopropylmethyl)-3-azabicyclo[3.1.0]hexane-3-carboxylate, 4

To a solution of 3 (1.68 g, 8.08 mmol) and cyclopropylmethyl bromide (1.31 g, 9.70 mmol) in toluene (25 mL) at 0° C. was added a solution of KHMDS (0.5 M in toluene, 17.8 mL, 8.89 mmol) and stirred for 18 h. The reaction was partially concentrated under vacuum and purified by column chromatography (silica gel) using 0 to 65% EtOAc in hexanes to 4a (minor diastereomer, 290 mg, 14%) and 4b (major diastereomer, 685 mg, 32%) as clear oils; ¹H-nmr (400 MHz, CDCl₃) δ (minor diastereomer) 3.60 (td, J=12.0, 4.0 Hz, 1H), 3.49 (d, J=12.0 Hz, 1H), 3.41 (d, J=12.0 Hz, 1H), 2.28-2.24 (m, 1H), 1.43 (s, 9H), 1.43-1.28 (m, 2H), 0.94-0.86 (m, 1H), 0.66-0.59 (m, 1H), 0.21 (q, J=6.0 Hz, 1H); LC-MS (214 nM) 3.18 min (>98%), m/z 207.1 [M-tBu]. ¹H-nmr (400 MHz, CDCl₃) δ (major diastereomer) 3.81 (d, J=12.0 Hz, 1H), 3.75 (d, J=12.0 Hz, 1H), 3.57 (td, J=12.0, 4.0 Hz, 1H), 1.83-1.78 (m, 2H), 1.43 (s, 9H), 1.46-1.40 (m, 2H), 0.92-0.84 (m, 1H), 0.61-0.52 (m, 2H), 0.22-0.16 (m, 2H); LC-MS (214 nM) 3.11 min (>98%), m/z 162.9 [M-Boc], 285.2 [M+Na].

f. Synthesis of 6-(cyclopropylmethyl)-3-(1-methyl-1n-imidazol-4-ylsulfonyl)-3-azabicyclo[3.1.0]hexane-6-carbonitrile, 5

To a solution of 4b (680 mg, 2.59 mmol) in CH₂Cl₂ (10 mL) was added TFA (2 mL) and stirred for 3 h. The reaction was concentrated under vacuum. Dissolved in CH₂Cl₂ (10 mL) and DIPEA (584 µL, 3.25 mmol), added 1-methylimidazole-4-sulfonyl chloride (466 mg, 2.59 mmol) and stirred for 18 h. The reaction was purified directly by column chromatography (silica gel) using 0 to 5% MeOH in CH₂Cl₂ to afford 5 (420 mg, 45%) as a white solid; ¹H-nmr (400 MHz, CDCl₃) δ 7.70 (s, 1H), 7.46 (s, 1H), 5.08 (br s, 2H), 3.90-3.80 (m, 2H), 3.75 (s, 3H), 3.62 (d, J=10.5 Hz, 2H), 1.93-1.89 (m, 2H), 1.39 (d, J=7.0 Hz, 2H), 0.88-0.79 (m, 1H), 0.55 (q, J=5.5 Hz, 2H), 0.16 (q, J=5.5 Hz, 2H); LC-MS (214 nM) 2.32 min, m/z 307.1 [M+H].

g. Amide Library

To a solution of 5 (410 mg, 1.34 mmol) in MeOH (30 mL) was added conc. NH₄OH (1 mL) and "Raney" Ni (50% w/w slurry in water, 100 mg). An atmosphere of H₂ (45 psi) was secured using a Parr hydrogenator and reacted for 18 h. The reaction was filtered through celite and concentrated under vacuum. The crude amine was dissolved in CH₂Cl₂ (20 mL) and DIPEA (480 µL, 2.68 mmol), placed into separated vials, added selected acid chloride (0.14 mmol) and reacted for 16 h. Added PS-trisamine (250 mg, 1.20 mmol/g, 0.30 mmol) and PS-isocyanate (250 mg, 1.05 mmol/g, 0.24 mmol) and agitated for 22 h. The reaction was filtered, concentrated and purified by mass directed preparative HPLC to provide amides 6a-j.

(1) 2,4-dichloro-n-((6-(cyclopropylmethyl)-3-(1-methyl-1n-imidazol-4-ylsulfonyl)-3-azabicyclo[3.1.0]hexan-6-yl)methyl)benzamide, 6a Using the above procedure, 2,4-dichloro-N-((6-(cyclopropylmethyl)-3-(1-methyl-1H-imidazol-4-ylsulfonyl)-3-azabicyclo[3.1.0]hexan-6-yl)methyl)benzamide, 6a, was prepared. ¹H-nmr (400 MHz, CDCl₃) (6a) δ 7.62 (d, J=8.0 Hz, 1H), 7.60 (br s, 1H), 7.45 (br s, 1H), 7.44 (d, J=2.0 Hz, 1H), 7.33 (dd, J=8.0, 2.0 Hz, 1H), 6.18 (br s, 1H), 3.77 (s, 3H), 3.72-3.66 (m, 2H), 3.52 (d, J=10.5 Hz, 2H), 3.47 (d, J=5.0 Hz, 2H), 1.68-1.62 (m, 2H), 1.24 (d, J=7.0 Hz, 2H), 0.88-0.79 (m, 1H), 0.46 (q, J=5.5 Hz, 2H), 0.09 (q, J=5.5 Hz, 2H); LC-MS (214 nM) 2.64 min (>98%), m/z 451.1 [M+H].

(2) Compounds 6b-6j

Compounds 6b-6j were prepared by procedures analogous to that used above.

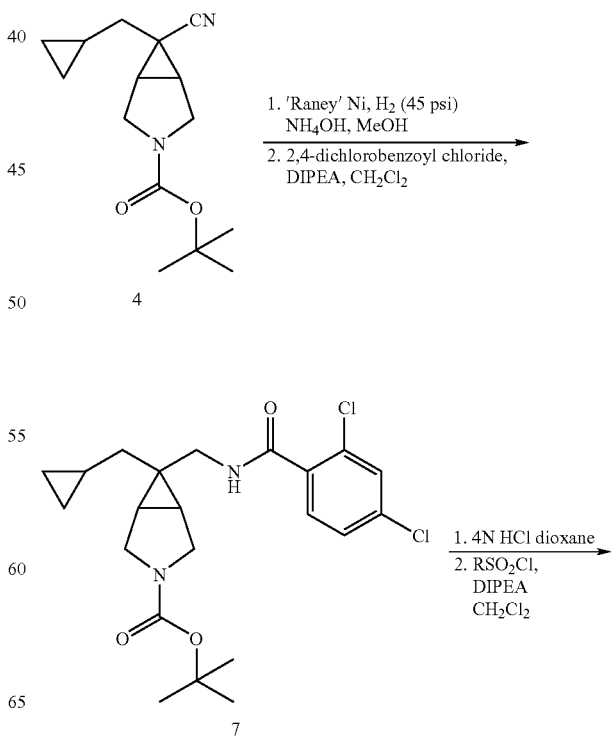

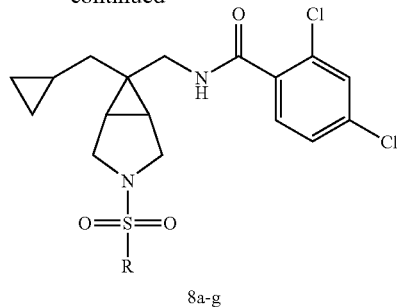

8a-g h. Synthesis of tert-butyl-6-((2,4-dichlorobenzamidon-ethyl)-6-(cyclopropylmethyl)-3-azabicyclo[3.1.0]hexane-3-carboxylate, 7

To a solution of 4 (850 mg, 3.24 mmol) in MeOH (20 mL) was added conc. NH$_4$OH (1.5 mL) and "Raney" Ni (50% w/w slurry in water, 200 mg). An atmosphere of H$_2$ (45 psi) was secured using a Parr hydrogenator and reacted for 18 h. The reaction was filtered through celite and concentrated under vacuum. The crude amine was dissolved in CH$_2$Cl$_2$ (8 mL) and DIPEA (613 µL, 3.50 mmol), added 2,4-dichlorobenzoyl chloride (678 mg, 3.24 mmol) and the reaction was stirred for 18 h. The reaction was purified directly by column chromatography (silica gel) using 0 to 70% EtOAc in hexanes to afford 7 (1.05 g, 74%) as a colorless oil; $^1$H-nmr (400 MHz, CDCl$_3$) δ 7.91 (d, J=8.0 Hz, 1H), 7.43 (d, J=1.5 Hz, 1H), 7.34 (dd, J=8.0, 1.5 Hz, 1H), 6.15 (br s, 1H), 3.80 (dd, J=14.0, 5.0 Hz, 1H), 3.62 (dd, J=11.5, 5.0 Hz, 1H), 3.55 (dd, J=11.5, 5.0 Hz, 1H), 3.52-3.40 (m, 3H), 1.67-1.57 (m, 2H), 1.44 (s, 9H), 1.34 (dd, J=14.5, 7.0 Hz, 1H), 1.18 (dd, J=14.5, 7.0 Hz, 1H), 0.81-0.70 (m, 1H), 0.53-0.44 (m, 2H), 0.11-0.03 (m, 2H).

i. Synthesis of Sulfonamide Library, 8a-g

To a solution of 7 (250 mg, 0.57 mmol) in 1,4-dioxane (1 ml) was added 4 N HCl in dioxane (2 mL) and stirred for 3 h. The reaction was concentrated under vacuum and the residue was dissolved in CH$_2$Cl$_2$ (1 mL) and DIPEA (244 µL, 1.36 mmol), placed into separated vials, added selected sulfonyl chloride (0.10 mmol) and reacted for 16 h. Added PS-trisamine (250 mg, 1.20 mmol/g, 0.30 mmol) and PS-isocyanate (250 mg, 1.05 mmol/g, 0.26 mmol) and agitated for 22 h. The reaction was filtered, concentrated and purified by mass directed preparative HPLC to provide amides 8a-g.

(1) 2,4-dichloro-n-(((6-(cyclopropylmethyl)-3-(cyclopropylmethylsulfonyl)-3-azabicyclo[3.1.0]hexan-6-yl)methyl) benzamide, 8d Using the above procedure, 2,4-Dichloro-N-(((6-(cyclopropylmethyl)-3-(cyclopropylmethylsulfonyl)-3-azabicyclo[3.1.0]hexan-6-yl)methyl)benzamide, 8d, was prepared. $^1$H-nmr (400 MHz, CDCl$_3$) (8d) δ 7.68 (d, J=8.0 Hz, 1H), 7.45 (s, 1H), 7.35 (d, J=8.0 Hz, 1H), 6.31 (br s, 1H), 3.83 (d, J=5.0 Hz, 2H), 3.74 (d, J=8.0 Hz, 2), 3.56 (d, J=10.0 Hz, 2H), 3.01 (d, J=8.0 Hz, 2H), 1.75-1.67 (m, 2H), 1.33 (d, J=6.5 Hz, 2H), 1.26-1.14 (m, 1H), 0.84-0.69 (m, 3H), 0.56-0.50 (m, 2H), 0.46-0.40 (m, 2H), 0.15-0.09 (m, 2H); LC-MS (214 nM) 2.53 min (>98%), m/z 457.1 [M+H].

(2) Compounds 8a-8c and 8e-8g

Compounds 8a-8c and 8e-8g were prepared by procedures analogous to that used above.

j. Compounds 9a-j
Library 9a-j was made in a similar manner to 8a-g.

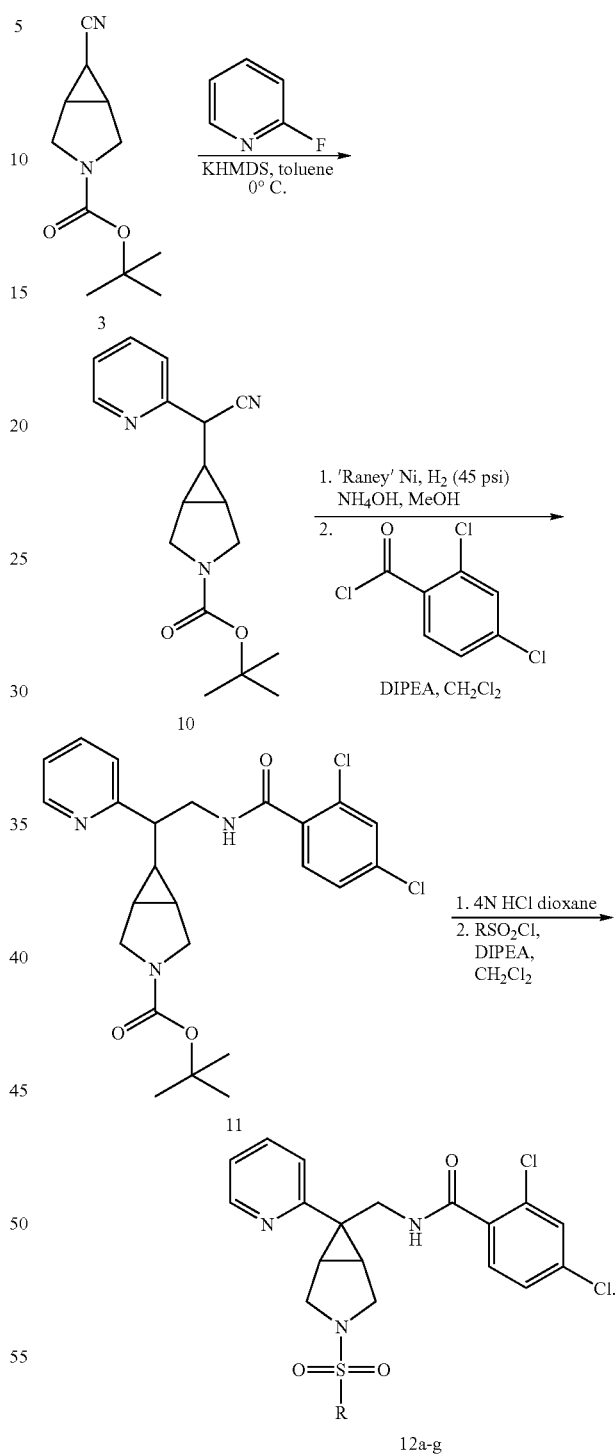

k. Synthesis of tert-butyl-6-cyano-6-(pyridine-2-yl)-3-azabicyclo[3.1.0]hexane-3-carboxylate, 10

To a solution of 3 (700 mg, 3.36 mmol) in toluene (16 mL) at 0° C. was added 2-fluoropyridine (326 mg, 3.36 mmol) and a solution of KHMDS (0.5M in toluene, 6.72 mL, 3.36 mmol). The reaction was warmed to room temperature and stirred for 18 h. The crude reaction was purified by column chromatography using 0 to 60% EtOAc in hexanes to afford 10 (390 mg, 41%) as a clear oil; $^{1}$H-nmr (400 MHz, CDCl$_{3}$) δ 8.46 (d, J=4.0 Hz, 1H), 7.75-7.66 (m, 2H), 7.17 (td, J=7.0, 1.5 Hz, 1H), 3.95 (d, J=12.5 Hz, 1H), 3.86 (d, J=12.5 Hz, 1H), 3.81-3.71 (m, 2H), 2.69 (s, 2H), 1.88 (d, J=5.0 Hz, 4H), 1.48 (s, 9H); LC-MS (214 nM) 2.96 min (>98%), m/z 286.1 [M+H].

l. Synthesis of tert-butyl-6-((2,4-dichlorobenzamidonethyl)-6-(pyridine-2-yl)-3-azabicyclo[3.1.0]hexane-3-carboxylate, 11

To a solution of 10 (320 mg, 1.12 mmol) in MeOH (10 mL) was added conc. NH$_{4}$OH (1 mL) and "Raney" Ni (50% w/w slurry in water, 100 mg). An atmosphere of H$_{2}$ (45 psi) was secured using a Parr hydrogenator and reacted for 18 h. The reaction was filtered through celite and concentrated under vacuum. The crude amine was dissolved in CH$_{2}$Cl$_{2}$ (4 mL) and DIPEA (610 µL, 2.46 mmol), added 2,4-dichlorobenzoyl chloride (280 mg, 1.34 mmol) and the reaction was stirred for 18 h. The reaction was purified directly by column chromatography (silica gel) using 0 to 65% EtOAc in hexanes to afford 11 (195 mg, 37%) as a white solid; $^{1}$H-nmr (400 MHz, CDCl$_{3}$) δ 8.48 (d, J=5.0 Hz, 1H), 7.64 (td, J=8.0, 1.5 Hz, 1H), 7.58 (d, J=8.0 Hz, 1H), 7.37 (d, J=1.5 Hz, 1H), 7.31-7.27 (m, 1H), 7.19 (d, J=8.0 Hz, 1H), 7.13 (dd, J=6.5, 6.0 Hz, 1H), 6.98 (br s, 1H), 4.08 (dd, J=14.5, 6.5 Hz, 1H), 3.86 (dd, J=14.5, 4.0 Hz, 1H), 3.79 (dd, J=12.0, 5.0 Hz, 1H), 3.73-3.67 (m, 3H), 2.30-2.19 (m, 2H), 1.50 (s, 9H); m/z 461.9 [M+H].

m. Synthesis of Sulfonamide Library, 12a-g

To a solution of 11 (190 mg, 0.41 mmol) in 1,4-dioxane (1 ml) was added 4 N HCl in dioxane (2 mL) and stirred for 3 h. The reaction was concentrated under vacuum and the residue was dissolved in CH$_{2}$Cl$_{2}$ (1 mL) and DIPEA (244 µL, 1.36 mmol), placed into separated vials, added selected sulfonyl chloride (0.10 mmol) and reacted for 16 h. Added PS-trisamine (250 mg, 1.20 mmol/g, 0.30 mmol) and PS-isocyanate (250 mg, 1.05 mmol/g, 0.26 mmol) and agitated for 22 h. The reaction was filtered, concentrated and purified by mass directed preparative HPLC to provide amides 12a-g.

Using the above procedure, 2,4-dichloro-N-((3-(1-methyl-1H-imidazol-4-ylsulfonyl)-6-(pyridine-2-yl)-3-azabicyclo[3.1.0]hexan-6-yl)methyl)benzamide, 12d, was prepared. $^{1}$H-nmr (400 MHz, CDCl$_{3}$) (12d) δ 7.70 (s, 1H), 7.66 (d, J=8.0 Hz, 1H), 7.47 (s, 1H), 7.45 (s, 1H), 7.32 (d, J=8.0 Hz, 1H), 6.31 (br s, 1H), 3.92 (d, J=10.0 Hz, 2H), 3.90-3.76 (m, 2H), 3.71-3.65 (m, 2H), 3.49 (s, 3H), 2.30-2.19 (m, 2H); m/z 506.1 [M+H].

n. Compounds 13a and 13b

Compounds 13a and 13b were made in an analogous manner to that used to prepare 12d. Using such procedure, 2-Trifluoromethyl-N-((6-(pyridin-2-yl)-3-(1-methyl-1H-imidazol-4-ylsulfonyl)-3-azabicyclo[3.1.0]hexan-6-yl)methyl)benzamide, 13b, was prepared. $^{1}$H-nmr (400 MHz, CDCl$_{3}$) (13b) δ 8.62 (d, J=5.5 Hz, 1H), 8.25 (td, J=8.0, 1.5 Hz, 1H), 7.88 (d, J=8.0 Hz, 1H), 7.69 (t, J=1.5 Hz, 1H), 7.59-7.27 (m, 6H), 3.93 (d, J=10.0 Hz, 2H), 3.89-3.79 (m, 2H), 3.73-3.67 (m, 2H), 3.50 (s, 3H), 2.30-2.19 (m, 2H); m/z 506.1 [M+H].

2. Cell Culture and Uptake Measurement

The procedure used was analogous to that disclosed in Williams, J. B.; Mallorga P. J.; Lemaire W.; Williams D. L.; Na S.; Patel S.; Conn J. P.; Pettibone D. J.; Austin C.; Sur C.; "Development of a scintillation proximity assay for analysis of Na+/Cl−-dependent neurotransmitter transporter activity," ANAL. BIOCHEM. 2003 Oct. 1; 321(1): 31-7.

Human placental choriocarcinoma cells (JAR cells, ATCC No. HTB-144) were obtained from the American Type Culture Collection (Manassas, Va.). JAR cells were cultured in 96-well Cytostar T plates (GE Healthcare No. RPNQ0162) in RPMI 1640 medium (Sigma-Aldrich) containing 10% fetal bovine serum, 10 mM HEPES, 1 mM sodium pyruvate, penicillin (100 µg/ml), and streptomycin (100 µg/ml). Cells were plated at a density of $1.3 \times 10^{4}$ cells/well and grown at 37° C. in a humidified atmosphere of 5% CO$_{2}$ for 40-48 h. Culture medium was removed from the Cytostar T plate and JAR cells were incubated with 30 µl of TB1A buffer (120 mM NaCl, 2 mM KCl, 1 mM CaCl$_{2}$, 1 mM MgCl$_{2}$, 10 mM Hepes, 5 mM L-alanine, pH 7.5 adjusted with 1 M Tris base) with or without multiple concentrations of test compound (added at 2× final concentration) for 1 min. Then 30 µl of [$^{14}$C]-glycine (Perkin-Elmer) diluted in TB1A was added to each well to give a final concentration of 10 µM. Cytostar T plates were then incubated in the dark at room temperature for 3 h, sealed with opaque white bottom plate seals (Perkin-Elmer) and clear top plate seals (Topseal A, Perkin-Elmer), and were counted on a Top Count (Packard). Glycine uptake was determined by measuring radioactivity in each well and plotted as a function of concentration of test compound. IC50 values were determined as the concentration of test compound that resulted in 50% maximal inhibition of glycine uptake. Nonspecific uptake of [$^{14}$C]-glycine was determined in the presence of 10 mM cold glycine. [$^{14}$C]-taurine (American Radiolabeled Chemicals, Inc.) uptake experiments were performed according to the same protocol except that 10 mM cold taurine was used to determine nonspecific uptake. For GlyT2 assays, COS-7 (ATCC No. CRL-1651) cells were utilized. COS-7 cells were transiently transfected with the human GlyT2 cDNA (Origene Technologies Inc., SC303452) using Fugene 6 (Roche) according to the manufacturer's instructions in Dulbecco's modified Eagle's medium (DMEM, Invitrogen) containing 10% Fetal Bovine Serum, 10 mM HEPES, 1 mM sodium pyruvate, penicillin (100 µg/ml), and streptomycin (100 µg/ml). The following day, the cells were plated at a density of $5 \times 10^{5}$ cells/well in Cytostar T plates and maintained at 37° C. in a humidified atmosphere of 5% CO$_{2}$ for 24 h. GlyT2 glycine uptake experiments were performed according to the same protocol previously described.

3. Potency Results for Exemplary 3.1.0 Bicyclic GlyT1 Inhibitors

The potency of exemplary disclosed compounds was established using the above-described procedure. The results are tabulated in Table 1.

TABLE 1
POTENCY RESULTS
| Compound | R | Potency | MW | M + H |
|---|---|---|---|---|
| 6a | 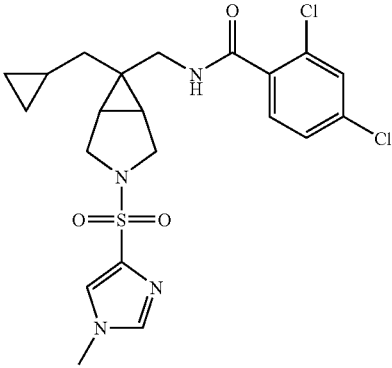 | 4.1 nM | 482.1 | 483.1 |
| 6b | 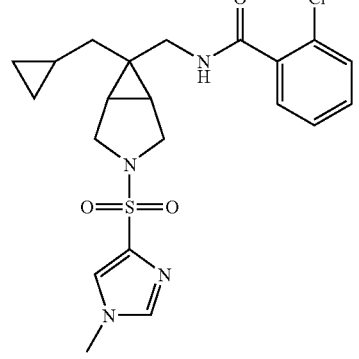 | 18.6 nM | 448.1 | 449.1 |
| 6c | 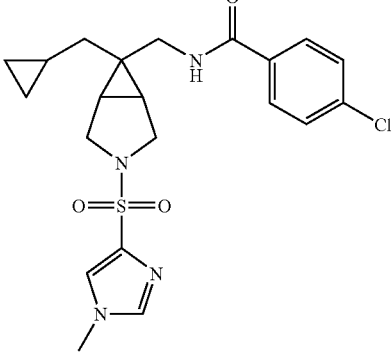 | 32 nM | 448.1 | 449.1 |
| 6d | 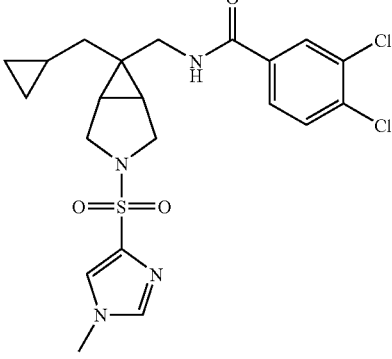 | 82 nM | 482.1 | 483.1 |

TABLE 1-continued

POTENCY RESULTS

| Compound | R | Potency | MW | M + H |
|---|---|---|---|---|
| 6e | | 4 nM | 450.2 | 451.2 |
| 6f | | 5 nM | 482.2 | 483.2 |
| 6g | | 64 nM | 482.2 | 483.2 |
| 6h | | 44 nM | 450.2 | 451.2 |

TABLE 1-continued
POTENCY RESULTS
| Compound | R | Potency | MW | M + H |
|---|---|---|---|---|
| 6i | 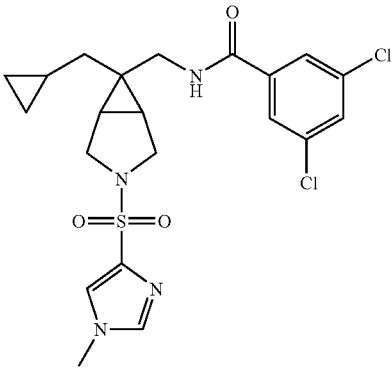 | 100 nM | 482.1 | 483.1 |
| 6j | 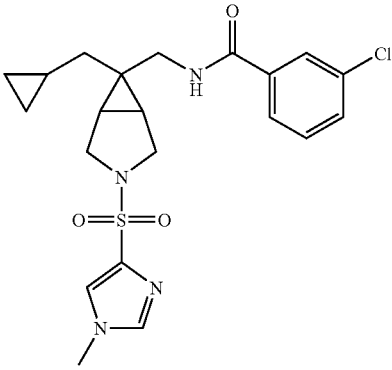 | 119 nM | 448.1 | 449.1 |
| 8a | 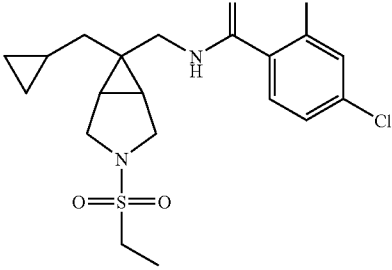 | 1.3 μM | 430.1 | 431.1 |
| 8b | 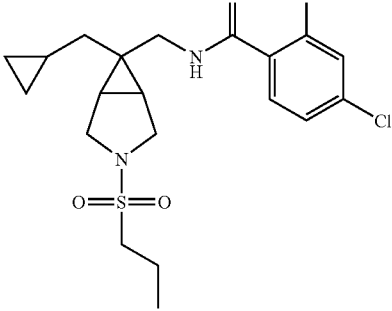 | 361 nM | 444.1 | 445.1 |

TABLE 1-continued
POTENCY RESULTS
| Compound | R | Potency | MW | M + H |
|---|---|---|---|---|
| 8c | 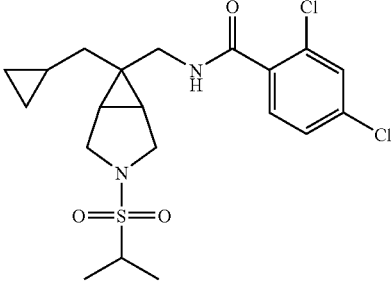 | 3.4 μM | 444.1 | 445.1 |
| 8d | 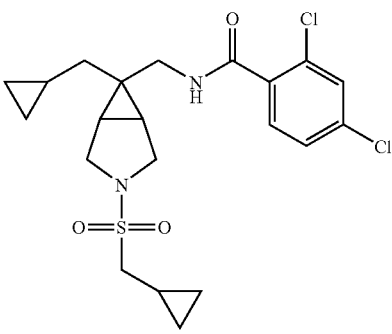 | 231 nM | 456.1 | 457.1 |
| 8e | 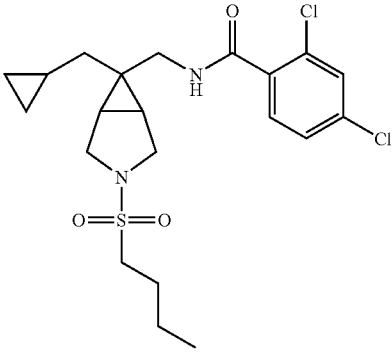 | 5.5 μM | 458.1 | 459.1 |
| 8e | 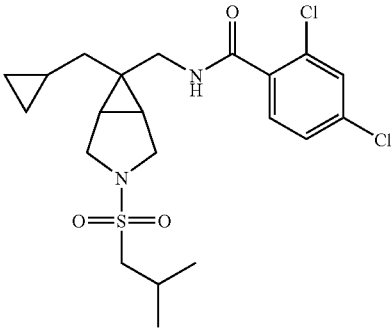 | 2.9 μM | 458.1 | 459.1 |

TABLE 1-continued

POTENCY RESULTS

| Compound | R | Potency | MW | M + H |
|---|---|---|---|---|
| 8f | | 1.0 μM | 478.1 | 479.1 |
| 8g | | 891 μM | 478.1 | 479.1 |
| 9a | | 2.1 μM | 394.2 | 395.2 |
| 9b | | 1.2 μM | 410.1 | 411.1 |

TABLE 1-continued

POTENCY RESULTS

| Compound | R | Potency | MW | M + H |
|---|---|---|---|---|
| 9c | | 1.85 μM | 410.1 | 411.1 |
| 9d | | 4.5 μM | 444.2 | 445.2 |
| 9e | | 1.1 μM | 444.2 | 445.2 |
| 9f | | 507 nM | 428.1 | 429.1 |

TABLE 1-continued

| Compound | R | Potency | MW | M + H |
|---|---|---|---|---|
| 9g | | 688 nM | 456.2 | 457.2 |
| 9h | | 629 nM | 456.2 | 457.2 |
| 9i | | 1.02 µM | 424.2 | 425.2 |
| 9j | | 1.02 µM | 424.2 | 425.2 |

TABLE 1-continued

POTENCY RESULTS

| Compound | R | Potency | MW | M + H |
|---|---|---|---|---|
| 12a | | >20 μM | 439.1 | 440.1 |
| 12b | | >20 μM | 453.1 | 454.1 |
| 12c | | >20 μM | 467.1 | 468.1 |
| 12d | | 240 nM | 505.1 | 506.1 |

TABLE 1-continued

POTENCY RESULTS

| Compound | R | Potency | MW | M + H |
|---|---|---|---|---|
| 12e | | >20 μM | 505.1 | 506.1 |
| 12f | | >20 μM | 501.1 | 502.1 |
| 12g | | >20 μM | 502.1 | 503.1 |
| 13a | | 457 nM | 471.1 | 472.1 |

TABLE 1-continued

POTENCY RESULTS

| Compound | R | Potency | MW | M + H |
|---|---|---|---|---|
| 13b | | 190 nM | 505.2 | 506.2 |

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

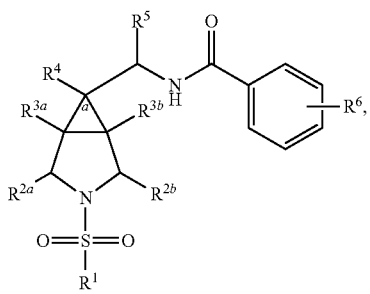

wherein $R^1$ is optionally substituted organic residue comprising 1 to 12 carbon atoms;

wherein each of $R^{2a}$ and $R^{2b}$ is independently selected from hydrogen, halogen, OR, nitrile, nitro, SR, $N(R)_2$, and optionally substituted organic residue having 1 to 6 carbons;

wherein each R is independently hydrogen or optionally substituted $C_{1-6}$ aliphatic, or two R groups on the same nitrogen are taken together with the nitrogen to form a 4-8 membered heterocyclic ring having 1-2 heteroatoms independently selected from nitrogen, oxygen, or sulfur;

wherein $R^{3a}$ and $R^{3b}$ are two substituents oriented in a syn geometry relative to each other, wherein $R^{3a}$ and $R^{3b}$ are independently selected from hydrogen and optionally substituted organic residue having 1 to 6 carbons;

wherein $R^4$ is selected from hydrogen, halogen, OR, cyano, nitro, SR, $N(R)_2$, and optionally substituted organic residue having 1 to 12 carbons;

wherein $R^5$ is two substituents and each is independently selected from hydrogen, halogen, OR, cyano, nitro, SR, $N(R)_2$, and optionally substituted organic residue comprising 1 to 6 carbons;

wherein $R^6$ is five substituents and each is independently selected from hydrogen, halogen, OR, cyano, nitro SR, $N(R)_2$, and optionally substituted organic residue comprising from 1 to 6 carbon atoms;

wherein the carbon at position "a" has a stereochemistry of R or S or a mixture thereof;

or a pharmaceutically acceptable salt thereof.

2. The compound of claim 1, wherein the carbon at position "a" has a stereochemistry of R or S.

3. The compound of claim 1, wherein $R^1$ is an optionally substituted group selected from C3-C12 mono cyclic or bicyclic cycloalkyl, C3-C12, mono cyclic or bicyclic cycloalkenyl, 3-12 membered monocyclic or bicyclic saturated or partially unsaturated heterocyclyl, phenyl, 8-10 membered aryl, and 5-6 membered heteroaryl having 1-4 heteroatoms independently selected from nitrogen, oxygen, or sulfur.

4. The compound of claim 1, wherein $R^{2a}$ and $R^{2b}$ are independently selected from hydrogen and optionally substituted organic residue having from 1 to 6 carbons.

5. The compound of claim 1, wherein $R^4$ is selected from C1-C12 alkyl or C2-C12 alkenyl or C2-C12 alkynyl, optionally substituted C1-C12 heteroalkyl or C2-C12 heteroalkenyl or C2-C12 heteroalkynyl, optionally substituted C3-C12 cycloalkyl or C3-C12 cycloalkenyl, optionally substituted C3-C12 heterocycloalkyl or C3-C12 heterocycloalkenyl, optionally substituted aryl, and optionally substituted heteroaryl.

6. The compound of claim 1, wherein each $R^5$ is hydrogen.

7. The compound of claim 1, wherein each $R^6$ is independently selected from hydrogen, halogen, and optionally substituted organic residue having from 1 to 6 carbons.

8. The compound of claim 1, wherein the compound inhibits GlyT1 receptor response to glycine as a decrease in response to non-maximal concentrations of glycine in JAR cells in the presence of the compound, compared to the response of equivalent JAR cells to glycine in the absence of the compound, having an $IC_{50}$ of less than about 100 μM.

* * * * *

UNITED STATES PATENT AND TRADEMARK OFFICE
CERTIFICATE OF CORRECTION

PATENT NO. : 8,497,289 B2
APPLICATION NO. : 12/648972
DATED : July 30, 2013
INVENTOR(S) : Lindsley et al.

It is certified that error appears in the above-identified patent and that said Letters Patent is hereby corrected as shown below:

In the Specifications:

In column 4, line 42, please delete "nitro SR" and insert --nitro, SR--;

In column 5, line 14, please delete "nitro SR" and insert --nitro, SR--;

In column 6, line 21, please delete "nitro SR" and insert --nitro, SR--;

In column 6, line 63, please delete "nitro SR" and insert --nitro, SR--;

In column 7, line 39, please delete "nitro SR" and insert --nitro, SR--;

In column 8, line 17, please delete "nitro SR" and insert --nitro, SR--;

In column 8, line 63, please delete "nitro SR" and insert --nitro, SR--;

In column 9, line 63, please delete "nitro SR" and insert --nitro, SR--;

In column 10, line 38, please delete "nitro SR" and insert --nitro, SR--;

In column 28, line 5, please delete "nitro SR" and insert --nitro, SR--;

In column 31, line 5, please delete "C3-C12, mono cyclic or bicyclic" and insert --C3-C12 mono cyclic or bicyclic--;

In column 33, line 3, please delete "nitro SR" and insert --nitro, SR--;

In column 34, line 16, please delete "C3-C12, mono cyclic or bicyclic" and insert --C3-C12 mono cyclic or bicyclic--;

In column 51, line 37, please delete "nitro SR" and insert --nitro, SR--;

In column 53, line 21, please delete "nitro SR" and insert --nitro, SR--;

In column 66, line 53, please delete "nitro SR" and insert --nitro, SR--;

In column 67, line 34, please delete "nitro SR" and insert --nitro, SR--;

In column 68, line 17, please delete "nitro SR" and insert --nitro, SR--;

In column 69, line 34, please delete "nitro SR" and insert --nitro, SR--;

In column 72, line 39, please delete "nitro SR" and insert --nitro, SR--;

Signed and Sealed this
Twenty-eighth Day of January, 2014

Michelle K. Lee
*Deputy Director of the United States Patent and Trademark Office*

CERTIFICATE OF CORRECTION (continued)
U.S. Pat. No. 8,497,289 B2

In column 74, line 44, please delete "nitro SR" and insert --nitro, SR--;

In the Claims:

In column 104, line 6, please delete "nitro SR" and insert --nitro, SR--;

In column 104, line 17, please delete "C3-C12, mono cyclic or bicyclic" and insert --C3-C12 mono cyclic or bicyclic--.